United States Patent
Hanson

(10) Patent No.: US 6,376,242 B1
(45) Date of Patent: Apr. 23, 2002

(54) METHODS AND COMPOSITIONS FOR TREATING PLATELET-RELATED DISORDERS USING MPL PATHWAY INHIBITORY AGENTS

(75) Inventor: Stephen R. Hanson, Stone Mountain, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/666,224

(22) Filed: Sep. 21, 2000

Related U.S. Application Data

(60) Provisional application No. 60/154,929, filed on Sep. 21, 1999.

(51) Int. Cl.$^7$ .............................. C12N 5/16; C12N 9/00; C12N 9/48; C12N 9/47
(52) U.S. Cl. .................. 435/334; 435/335; 435/337; 435/343; 435/214; 424/94.1; 424/192.1; 424/195.11; 424/94.63
(58) Field of Search ................... 514/822, 834, 514/964; 424/172.1, 173.1; 435/334, 335, 337, 343

(56) References Cited

U.S. PATENT DOCUMENTS

| | | |
|---|---|---|
| 3,932,407 A | 1/1976 | Beverung, Jr. et al. |
| 4,088,753 A | 5/1978 | Parmer |
| 4,146,718 A | 3/1979 | Jenks et al. |
| 4,206,214 A | 6/1980 | Harker et al. |
| RE31,617 E | 6/1984 | Beverung, Jr. et al. |
| 4,743,445 A * | 5/1988 | Delwiche et al. |
| 4,847,276 A | 7/1989 | Yarrington |
| 5,185,323 A | 2/1993 | Gewirtz |
| 5,306,709 A | 4/1994 | Gewirtz |
| 5,391,557 A | 2/1995 | Cullinan et al. |
| 5,440,020 A | 8/1995 | Coller |
| 5,498,599 A * | 3/1996 | Choi et al. |
| 5,506,107 A | 4/1996 | Cunningham et al. |
| 5,572,944 A | 11/1996 | Gewirtz et al. |
| 5,620,960 A | 4/1997 | Arnold et al. |
| 5,756,083 A | 5/1998 | Elliott |
| 5,789,539 A | 8/1998 | Daly et al. |
| 5,830,647 A | 11/1998 | Eaton et al. |
| 5,969,451 A | 2/1999 | Dower et al. |
| 5,932,546 A | 8/1999 | Barrett et al. |
| 6,008,232 A | 12/1999 | Lakshmanan |
| 6,103,740 A * | 8/2000 | Lakshmanan |

FOREIGN PATENT DOCUMENTS

| | | |
|---|---|---|
| EP | 0 904 783 | 3/1999 |
| WO | WO 96/25498 | 8/1996 |
| WO | WO 96/40750 | 12/1996 |
| WO | WO 97/28190 | 8/1997 |
| WO | WO 99/08524 | 2/1999 |
| WO | WO 99/08525 | 2/1999 |
| WO | WO 99/10494 | 4/1999 |

OTHER PUBLICATIONS

Landolfi et al., "Aspirin in Polycythemia Vera and Essential Thrombocythemia: Cuurent facts adn Perspectives", Leukemia and Lymphoma, 1996, vol. 22, Suppl. 1 p. 83–86.*

Broudy et al., "Thrombopoietin Stimulates Colony–Forming Unit–Megakaryocyte Proliferation and Megakaryocyte Maturation Independently of Cytokines that Signal through the gp130 Receptor Subunit", Blood, 1996, vol. 8, No. 6, p. 2026–2032.*

Harker, et al., "Regulation of Platelet Production and Function by Megakaryocyte Growth and Development Factor in Nonhuman Primates", Blood, vol. 87, No. 5, pp. 1833–1844, (1996).

Harker, "Platelets in Thrombotic Disorders: Quantitative and Qualitative Platelet Disorders Predisposing to Arterial Thrombosis", Seminars in Hematology, vol. 35, No. 3, pp. 241–252, (1998).

van der Loo, et al. "A Role for Changes in Platelet Production in the Cause of Acute Coronary Syndromes", Arterioscler Thromb Vasc Biol., vol. 19, pp. 672–679 (1999).

Al–Jibouri, L.M. and Najim, R.A., "Effect of dipyridamole on blood glucose and liver cyclic AMP levels and platelet count during endotoxaemia in mice", *Clin. Exp. Pharmacol. Physiol.*, 15(7):527–32 (1988) Abstract.

Andes, et al., "Inhibition of platelet production induced by an antiplatelet drug, anagrelide, in normal volunteers", *Thromb Haemost.*, 52(3):325–8 (1984).

Balan, K.K and Critchley, M., "Outcome of 259 patients with primary proliferative polycythaemia (PPP and idiopathic thrombocythaemia (IT) treated in a regional nuclear medicine department with phosphoru 32—a 15 year review", *Br. J. Radiol.*, 70(839):1169–73 (1997) Abstract.

Balduini, et al., "Effect of anagrelide on platelet count and function in patients with thrombocytosis and myeloproliferative disorders", *Haematologica*, 77(1):40–3 (1992) Abstract.

Barnathan, et al., "Aspirin and dipyridamole in the prevention of acute coronary thrombosis complicatin coronary angioplasty", *Circulation*, 76(1):125–134 (1987).

Bellucci, et al., "Positive and negative regulation of megakaryocytopoiesis", *C.R. Seances Soc. Biol. Fil.* 190(5–6):515–32 (1996) Abstract.

(List continued on next page.)

Primary Examiner—Leon B. Lankford, Jr.
Assistant Examiner—Ruth A. Davis
(74) Attorney, Agent, or Firm—Wolf, Greenfield & Sacks, P.C.

(57) ABSTRACT

The invention relates to the treatment of subjects for the purpose inhibiting vaso-occlusive events, including thrombosis and embolism, by administering agents which reduce the number of circulating platelets to low or below normal levels. Methods and pharmaceutical preparations comprising such agents are provided.

47 Claims, No Drawings

OTHER PUBLICATIONS

Bunn, H.F., "Pathophysiology of the anemias", *Harrison's Principles of Internal Medicine: Hematology and Oncology*, 1514, 1566–67 New York, McGraw–Hill, 1991.

Cazenave, J.P. and Gachet, C., "Anti–platelet drugs: do they affect megakaryocytes?", *Baillieres Clin Haematol,* 10(1):163–80 (1997).

Chen, et al., "Thrombospondin, a negative modulator of megakaryocytopoiesis", *J. Lab. Clin. Med.,* 129(2):231–8 (1997) Abstract.

Cortelazzo, et al., "Hydroxyurea for patients with essential thrombocythemia and a high risk of thrombosis", *N. Engl. J. Med.,* 332(17):1132–6 (1995) Abstract.

Dale, et al., "Chronic thrombocytopenia is induced in dogs by development of cross–reacting antibodies the MpL ligand", *Blood,* 90(9):3456–3461 (1997).

Davies, et al., "Adverse events reported by postmenopausal women in controlled trials with raloxifene" *Obstetrics & Gynecology,* 93(4):558–565 (1999).

De Serres, et al., "Immunogenicity of thrombopoietin mimetic peptide GW395058 in BALB/c mice and New Zealand white rabbits:evaluation of the potential for thrombopoietin neutralizing antibody product in man", *Stem Cells,* 17:203–209 (1999).

Deng, et al., "A monoclonal antibody cross–reactive with human platelets, megakaryocytes, and commo acute lymphocytic leukemia cells", *Blood,* 61(4):759–764 (1983).

Gaver, et al., "Disposition of anagrelide, an inhibitor of platelet agregation", *Clin. Pharmacol. Ther.,* 29(3):381–6 (1981) Abstract.

Gewirtz, et al., "Cell–mediated suppression of megakaryocytopoiesis in acquired amegakaryocytic thrombocytopenic purpura", *Blood,* 68(3):619–26 (1986) Abstract.

Glushkov, et al., "Changes in hemostatic system indices during hemosorption in healthy dogs", *Biull E Biol. Med.,* 94(7):95–8 (1982) Abstract.

Goldberg, et al., "Thrombocytotic suppression of megakaryocyte production from stem cells", *Blood,* 49(1):59–69 (1977) Abstract.

Gugliotta, et al., "In vivo and in vitro inhibitory effect of alpha–interferon on megakaryocyte colony growth in essential thrombocythaemia", *Br. J. Haematol.,* 71(2):177–81 (1989) Abstract.

Herron, et al., "Inhibition of megakaryocytic colonies in vitro by anagrelide", *Clin. Res.,* 34(2):459A (1986) Abstract.

Hung, et al., "Focused antithrombotic therapy: novel anti–platelet salicylates with reduced ulcerogenic potential and higher first–pass detoxification than aspirin in rats", *J. Lab. Clin. Med.,* 132(6):469–77 (1 Abstract.

Jones, et al., "Inhibitors of cyclic AMP phosphodiesterase. 1. Analogues of cilostamide and anagrelide", *J. Med. Chem.,* 30(2):295–303 (1987) Abstract.

Lecomte–Raclet, et al., "New insights into the negative regulation of hematopoiesis by chemokine platelet factor 4 and related peptides", *Blood,* 91(8):2772–80 (1998) Abstract.

Ludwig, et al., "Interferon–alfa corrects thrombocytosis in patients with myeloproliferative disorders", *Cancer Immunol. Immunother.,* 25(3):266–73 (1987) Abstract.

Mazur, et al., Analysis of the mechanism of anagrelide—induced thrombocytopenia in humans, *Blood,* 79(8):1931–1937 (1992).

Mazzucconi, et al., "Pipobroman therapy of essential thrombocythemia", *Scand J. Haematol.,* 37(4):306–9 (1986) Abstract.

Mazzucconi, et al., "Therapy with Anagrelide in patients affected by essential thrombocythemia: preliminary results", *Haematologica,* 77(4):315–7 (1992) Abstract.

McCune, et al., "Precipitous fall in platelet count with anagrelide: case report and critique of dosing recommendations", *Pharmacotherapy,* 17(4):822–6 (1997) Abstract.

Meanwell, et al., "Inhibitors of blood platelet cAMP phosphodiesterase. 2. Structure–activity relationships associated with 1,3–dihydro–2H–imidazo[4,5–b]quinolin–2–ones substituted with functionalized side chains", *J. Med. Chem.,* 35(14):2672–87 (1992) Abstract.

Nagae, S. and Hori, Y., "Immune thrombocytopenia due to Tranilast (Rizaben): detection of drug–dependent platelet–associated IgG", *J. Dermatol.,* 25(11):706–9 (1998).

Negrev, et al., "Influence of nonselective beta–adrenergic impacts on the effects of thrombocytopoietin in mice", *Acta Physiologica et Pharmacologica Bulgaria,* 13:1:35–39 (1987).

Ramires, et al., "Effect of ticlopidine and dipyridamole on platelet aggregation and count in patients with chronic stable angina pectoris", *Arq Bras. Cardiol.,* 56(4):323–7 (1991) Abstract.

Robak, T, et al., "Anagrelide—new antiplatelet drug", *Acta Haematol Pol.,* 25(4):309–15 (1994) Abstract.

Sato, et al., "Multivariate analysis of risk factors for thrombus formation in University of Tokyo ventricular assist device", *J. Thorac. Cardiovasc. Surg.,* 106:520–7 (1993).

Scott, et al., "Local delivery of an antithrombin inhibits platelet–dependent thrombosis", *Circulation,* 90(4):1951–1955 (1994).

Seiler, et al., "Effects of anagrelide on platelet cAMP levels, cAMP–dependent protein kinase and thrombin–induced $Ca^{++}$ fluxes", *J. Pharmacol Exp. Ther.,* 243(2):767–74 (1987) Abstract.

Shinagawa, et al., "Allopurinol induced pancytopenia in a patient with myeloproliferative disorder", *Rinsho Ketsueki,* 38(1):64–71 (1997) Abstract.

Smith, J.B. "Effect of thromboxane synthetase inhibitors on platelet function: enhancement by inhibition of phosphodiesterase", *Thromb. Res.,* 15:28(4):477–85 (1982) Abstract.

Solberg, et al., "The effects of anagrelide on human megakaryocytopoiesis", *Br. J. Haematol.,* 99(1):174–80 (1997) Abstract.

Thaulow, et al., "Blood platelet count and function are related to total and cardiovascular death in apparently healthy men", *Circulation* 84(2):613–617 (1991).

Trowbridge, et al., "Platelet production in myocardial infarction and sudden cardiac death", *Thromb. Haemost,* 52(2):167–171 (1984).

Van de Pette, "Primary thrombocythaemia treated with busulphan", *Br. J. Haematol.,* 62(2):229–37 (1986) Abstract.

van der Loo, et al., "Megakaryocytes and platelets in vascular disease", *Bailliere's Clinical Haematology,* 10(1):109–123 (1997).

Venuti, et al., "Inhibitors of cyclic AMP phosphodiesterase. 3. Synthesis and biological evaluation of pyrido and imidazolyl analogues of 1,2,3,5–tetrahydro–2–oxoimidaze[2,1–b] quinazoline", *J. Med. Chem.*, 31(11):2136–45 (1988) Abstract.

Wada, et al., "Characterization of the truncated thrombopoietin variants", *Biochem. Biophys. Res. Comm.*, 213(3):1091–1098 (1995).

Wadenvik, et al., "The effect of alpha–interferon on bone marrow megakaryocytes and platelet production rate in essential thrombocythemia", *Blood,* 77(10):2103–8 (1991) Abstract.

Wilhelmsen, L., "Thrombocytes and coronary heart disease", *Circulation* 84(2):936–938 (1991).

Yataganas, et al., "alpha Interferon treatment of essential thrombocythaemia and other myeloproliferative disorders with excessive thrombocytosis", *Eur. J. Cancer,* 27 Suppl 4:S69–71 (1991) Abstract.

Yeager, et al., "Effects of cyclophosphamide on murine bone marrow and splenic megakaryocyte–CFC, granulocyte–macrophage–CFC, and peripheral blood cell levels", *J. Cell. Physiol.,* 112(2):222–8 (1982) Abstract.

* cited by examiner

METHODS AND COMPOSITIONS FOR TREATING PLATELET-RELATED DISORDERS USING MPL PATHWAY INHIBITORY AGENTS

RELATED APPLICATIONS

This application claims priority to U.S. Provisional Patent Application filed September 21, 1999, entitled "METHODS AND COMPOSITIONS FOR TREATING PLATELET-RELATED DISORDERS", Ser. No. 60/154,929, the contents of which are incorporated by reference herein in their entirety.

FIELD OF THE INVENTION

The invention relates to methods and products for treatment and/or prevention of platelet related thrombotic and other vaso-occlusive disorders.

BACKGROUND OF THE INVENTION

Conditions resulting from thrombotic or thromboembolic events are the leading causes of illness and death in adults in western civilization. A great deal of effort and monetary resources have been directed towards understanding the mechanisms involved in vascular occlusive diseases involving thrombotic and thromboembolic events. These efforts have yielded a number of promising therapeutic agents. Notwithstanding the effort and financial resources that have been invested, these conditions still account for the vast majority of illness and death in the adult populations of developed nations.

Platelets are an important cellular component of blood involved in hemostasis as well as thrombotic or thromboembolic events. Abnormally high platelet counts such as those that result from hematological proliferative disorders such as for example essential thrombocythemia have been recognized as an important risk factor in thrombus formation. Furthermore, it has long been accepted that aspirin, which is known to inhibit cyclooxygenase and thereby prevents production of thromboxane $A_2$ in platelets, lowers the incidence of a thrombotic or thromboembolic events. The mechanism through which aspirin exerts its therapeutic effect however is controversial since in addition to affecting platelets, aspirin is also known to possess anti-inflammatory properties. Therapeutic regiments thus far reported have as their aim an inhibition of platelet function (e.g., inhibition of platelet adhesion, aggregation or factor release) or a reduction in platelets count in patients with abnormally high levels in certain hematological malignancies to levels approximating normal levels. Therapeutic intervention for reducing platelet count to low normal or below normal levels in subjects without myeloproliferative disorders has not been proposed primarily since normal platelet count has been thought to be critical to normal hemostasis.

SUMMARY OF THE INVENTION

The invention in a broad aspect involves the surprising discovery that subjects, including those with normal levels of circulating platelets, can unexpectedly derive medical benefit from a reduction in platelet count to below normal levels, without serious adverse consequences as a result of the platelet count reduction. The benefit may be proportional or correlative to the reduction in platelet count in a broad safety range. Thus in situations where it is desirable to inhibit a pathological condition or process mediated in part by normal levels of circulating platelets, subjects can be treated to lower platelet count preferably to a below normal level, thereby inhibiting the development, progression or propagation of the condition or accelerating or enhancing its regression. The methods of the invention are also useful for reducing the incidence of abnormal vessel growth induced by the presence of platelets.

A method is provided for treating a subject to reduce the risk of developing an adverse condition or to inhibit the progression and consequences of an adverse condition mediated at least in part by platelets. In some aspects, the subject is treated to reduce platelet count to low normal levels, while in other aspects the subject is treated to reduce platelet count to below normal levels. In one embodiment, the subject is treated with a pharmaceutical agent.

In preferred embodiments, the agent is an MPL (myeloproliferative leukemic) pathway inhibitory agent. An MPL pathway inhibitory agent is an agent that interferes with the MPL pathway. The MPL pathway is the set of events which start when a MPL ligand binds to a MPL receptor and which effect an increase in platelet count and platelet maturation. The pathway includes ligand-receptor binding, intracellular signaling events, and modulation of gene expression (such as antisense molecules). An MPL pathway inhibitory agent may be selected from the group consisting of an agent that binds to MPL ligand and thereby interferes with the ability of MPL ligand to bind MPL receptor, an agent that binds to MPL receptor and thereby interferes with the ability of MPL receptor to bind to MPL ligand or interferes with the ability of MPL receptor to transduce a signal to another molecule in the MPL pathway, and an agent that binds to an intracellular cell signaling compound that relays a signal from the MPL receptor, but is not so limited. In important embodiments, the agent is one which binds to an MPL receptor or one which binds to a thrombopoietin molecule. The agent is not anagrelide nor an anagrelide derivative.

In one aspect, the invention provides a method for treating a subject to inhibit a vaso-occlusive event. Inhibiting a vaso-occlusive event means to prevent the formation of a vaso-occlusive event, to reduce progression and consequences of an already established vaso-occlusive event or to induce regression of a vaso-occlusive event. The invention also provides other methods aimed at reducing morbidity or mortality of subjects from vaso-occlusive events such as but not limited to thrombotic events which may lead to total or partial vessel blockage by thrombus, or arterial stenosis due to excessive cell proliferation.

The methods of the invention comprise administering to a subject in need of such treatment an agent that reduces platelet count in the subject. The agent is administered in an amount effective to reduce platelet count in the subject to at least a low normal level. Such reductions in platelet count will reduce morbidity and/or mortality and thereby provide patient outcome benefit.

As used herein, a vaso-occlusive event includes a pathological partial occlusion (including a narrowing) or complete occlusion of a blood vessel, a stent or a vascular graft. A vaso-occlusive event intends to embrace thrombotic or thromboembolic events, and the vascular occlusion disorders or conditions to which they give rise. Thus, a vaso-occlusive event is intended to embrace all vascular occlusive disorders resulting in partial or total vessel occlusion from thrombotic or thromboembolic events, except those that are related to high platelet count due to a hematological proliferative disorder. A thrombotic event as used herein is meant to embrace both a local thrombotic event and a distal thrombotic event (e.g., a thromboembolic event such as for example an embolic stroke). A vaso-occlusive event also includes abnormal blood vessel growth induced by the presence of platelets and the factors they secrete. An example of this latter form of vaso-occlusive event is intimal hyperplasia which results in a narrowing of the blood vessels (i.e., reduction in the diameter of blood vessels either locally or throughout an extended segment of the vessel) due to a hyperproliferation of cells of the intimal layer of the blood vessel wall.

Preferably, the subject is otherwise free of symptoms calling for treatment with the agent. In some embodiments, the subject is preferably free of symptoms associated with a hematological proliferative disorder such as for example myeloproliferative disease. Preferably, the subject is a human subject, but is not so limited. In another embodiment, the subject is apparently healthy. In preferred embodiments, the subjects do not have abnormally elevated platelet levels (i.e., a platelet count that is higher than the normal range) that are caused by a hematological proliferative disorder. Thus, preferably, the subjects do not have a hematological proliferative disorder. In an important embodiment, the subject has a normal platelet count prior to treatment. In some embodiments, the subject has a higher platelet count than the mean normal level but is still considered within the normal range. As an example, a subject with a platelet count of 450×103 platelets per $\mu$l is considered to be at the high end of the normal range and is intended to be treated by the methods of the invention. In some embodiments, the subject may have a platelet count above the usual range, but without any underlying hematological proliferative disorder. In still other aspects of the invention, the subject is one who has a hematological proliferative disorder and the methods of the invention intend to reduce the risk of a vaso-occlusive event in such a subject.

In some aspects, the invention intends to treat subjects who are at risk of a vaso-occlusive event. These subjects may or may not have had a previous vaso-occlusive event. The invention embraces the treatment of subjects prior to a vaso-occlusive event, at a time of a vaso-occlusive event and following a vaso-occlusive event. Thus, as used herein, the "treatment" of a subject is intended to embrace both prophylactic and therapeutic treatment, and can be used both to limit or to eliminate altogether the symptoms or the occurrence of a vaso-occlusive event. In one embodiment, the subject may exhibit symptoms of a vaso-occlusive event.

The invention also intends to embrace the treatment of a subject that has an abnormally elevated risk of a vaso-occlusive event such as a thrombotic event. The subject may have vascular disease. The vascular disease may be selected from the group consisting of arteriosclerosis, cardiovascular disease, cerebrovascular disease, renovascular disease, mesenteric vascular disease, pulmonary vascular disease, ocular vascular disease or peripheral vascular disease.

In another embodiment, the subject has had a primary vaso-occlusive event such as a primary thrombotic event. The agent may be administered to a subject following a primary vaso-occlusive event. The method of the invention embraces treatment of a subject to reduce the risk of a secondary thrombotic event or to inhibit the propagation of an existing thrombotic event. The thrombotic event may be selected from the group consisting of arterial thrombosis, coronary thrombosis, heart valve thrombosis, coronary stenosis, stent thrombosis and graft thrombosis. The vaso-occlusive event also includes disorders or conditions that may arise from a thrombotic event or a thromboembolic event and in this regard a vaso-occlusive event includes but is not limited to myocardial infarction, stroke and transient ischemic attack. In an important embodiment the vaso-occlusive event is myocardial infarction. In one embodiment, the subject has had a myocardial infarction. A subject who has hypercholesterolemia, hypertension or atherosclerosis also can be treated by the methods of the invention.

In yet another embodiment, the subject is one who will undergo an elective surgical procedure. The agent may be administered to such a subject prior to the elective surgical procedure. The method of the invention can also be directed towards a subject who has undergone a surgical procedure. As used herein, a surgical procedure is meant to embrace those procedures that have been classically regarded as surgical procedures as well as interventional cardiology procedures such as arteriography, angiography, angioplasty and stenting. Thus, the surgical procedure, whether elective or not, can be selected from the group consisting of coronary angiography, coronary stent placement, coronary by-pass surgery, carotid artery procedure, peripheral stent placement, vascular grafting, thrombectomy, peripheral vascular surgery, vascular surgery, organ transplant, artificial heart transplant, vascular angioplasty, vascular laser therapy, vascular replacement, prosthetic valve replacement and vascular stenting.

In one embodiment, the agent is administered in an amount effective to reduce the platelet count to at least low normal levels if the subject has a normal platelet count prior to treatment. In another embodiment, the agent is administered in an amount effective to reduce In some embodiments, the agent is administered in an amount effective to reduce the platelet count to below normal levels if the subject has an above normal platelet count prior to treatment. In these latter embodiments, the subject may not have a hematological proliferative disorder, but is not so limited.

The MPL pathway inhibitory agent is administered in an amount effective to reduce platelet count, in the subject, preferably to below normal levels. In some embodiments, the MPL pathway inhibitory agent is administered in amounts effective to reduce the platelet count to low normal levels.

Depending upon the particular embodiment, the platelet count is reduced anywhere from at least 10% to 95% of pre-treatment levels. In particular embodiments, the platelet count is reduced by at least 90%, at least 80%, at least 70%, at least 60%, at least 50%, at least 40%, at least 30%, at least 20%, or at least 10%. In some important embodiments, the platelet count is reduced by more than 10%. In another embodiment, platelet count is reduced by more than 30% or by more than 40%.

In some embodiments that embrace the treatment of a human subject, platelet count is preferably reduced to below 200×10$^3$ platelets per $\mu$l, and in still others to below 150×10$^3$ platelets per $\mu$l. In still another embodiment, platelet count is reduced to below 100×10$^3$ platelets per $\mu$l of blood in a human subject. In embodiments in which the platelet count is reduced to a low normal level this is defined as 10% less than the mean normal platelet count. In other embodiments, the platelet count is reduced to below normal levels.

In yet another embodiment, the agent is administered in an amount effective to reduce the platelet count by at least 10% and to an amount above 200×10$^3$ platelets per $\mu$l. In other embodiments, the agent is administered in an amount effective to reduce the platelet count by at least 10% and below 200×10$^3$ platelets per $\mu$l. In other embodiments, the agent is administered in an amount effective to reduce the platelet count by at least 20% and to below 200×10$^3$ platelets per $\mu$l.

The agent of the invention can be administered simultaneously or consecutively with another therapeutic compound such as an agent which would normally be indicated for the subject. Such agents include agents for treating vascular disease or vascular complications (i.e., complications resulting from such disease). In some important embodiments, the agent for treating vascular disease or vascular complications is an anti-thrombotic agent. The anti-thrombotic agent may be selected from the group consisting of an anti-coagulant agent, a fibrinolytic agent and an inhibitor of platelet function, but is not so limited. Thus, in one embodiment, the agent is administered with an inhibitor of platelet function. The inhibitor of platelet function may be selected from the group consisting of aspirin, abciximab, clopidogrel and dipyridamole. In another embodiment, the agent may be administered with an anti-coagulant agent. The anti-coagulant may be selected from the group consisting of glycosaminoglycans (e.g., heparins) and vitamin K antagonists. In a further embodiment, the agent is administered with a fibrinolytic agent, such as but not limited to one selected from the group consisting of plasminogen activators such as tissue plasminogen activator (TPA), streptokinase and urokinase, plasmin and plasminogen. Depending upon the embodiment, the agent of the invention may be administered before, simultaneously with or following administration of the agent for treating vascular disease or vascular complications.

In one embodiment, the agent is administered following a primary vaso-occlusive event such as a thrombotic event. The agent can be administered in a number of ways, including enteral and parenteral routes. In some preferred embodiments, the agent is administered in a sustained release device.

The invention also provides a number of pharmaceutical preparations comprising agents that reduce platelet count. The pharmaceutical preparations of the invention comprise one or more agents that reduce platelet count and a pharmaceutically acceptable carrier. The agent is present in the pharmaceutical preparation in an amount effective to reduce platelet count. In important embodiments of the invention, the pharmaceutical preparation comprises the agent in an amount effective to reduce platelet count to low normal levels or to below normal levels.

In yet a further aspect, the invention provides a sustained release device that comprises an agent that reduces platelet count in a subject, wherein the agent is released for at least 7 days. In one embodiment, the sustained release device further comprises a an agent for treating vascular disease or vascular complications. The agent for treating vascular disease or vascular complications may be an anti-thrombotic agent but is not so limited. In one embodiment, the anti-thrombotic is selected from the group consisting of an anti-coagulant agent, a fibrinolytic agent and an inhibitor of platelet function.

Other useful categories of such agents include but are not limited to anti-inflammatory agents, anti-thrombotic agents, anti-platelet agents, fibrinolytic agents, lipid reducing agents, direct thrombin inhibitors, glycoprotein IIb/IIIa receptor inhibitors, agents that binds to cellular adhesion molecules and inhibit the ability of white blood cells to attach to such molecules, calcium channel blockers, beta-adrenergic receptor blockers, cyclooxygenase-2 inhibitors, and angiotensin system inhibitors.

In one embodiment, the MPL pathway inhibitory agent is administered following a primary vaso-occlusive event such as a thrombotic event. The MPL pathway inhibitory agent can be administered in a number of ways, including enteral and parenteral routes. In some preferred embodiments, the MPL pathway inhibitory agent is administered orally. In other preferred embodiments, the MPL pathway inhibitory agent is administered in a sustained release device.

The invention also provides a number of pharmaceutical preparations comprising the MPL pathway inhibitory agent. In one aspect, pharmaceutical preparations are provided each of which comprise an agent that inhibits signal transduction from an MPL receptor, or an agent that binds to an MPL receptor, or an agent that binds to an extracellular region of the MPL receptor, or an agent that binds to an intracellular region of the MPL receptor, or an agent that binds to a thrombopoietin molecule, or an agent that inhibits the binding of a thrombopoietin molecule to an MPL receptor. The pharmaceutical preparations of the invention comprise at least one of the foregoing agents and a pharmaceutically acceptable carrier. The MPL pathway inhibitory agent is present in the pharmaceutical preparation in an amount effective to reduce platelet count in a subject. In important embodiments of the invention, the pharmaceutical preparation comprises the MPL pathway inhibitory agent in an amount effective to reduce platelet count to low normal or below normal levels.

In yet a further aspect, the invention provides a sustained release device that comprises the MPL pathway inhibitory agent, and wherein the MPL pathway inhibitory agent is released for at least 7 days. In one embodiment, the agent is administered following a primary vaso-occlusive event such as a thrombotic event. The agent can be administered in a number of ways, including enteral and parenteral routes. In some preferred embodiments, the agent is administered in a sustained release device.

The invention also provides a number of pharmaceutical preparations comprising agents that reduce platelet count. The pharmaceutical preparations of the invention comprise one or more agents that reduce platelet count and a pharmaceutically acceptable carrier. The agent is present in the pharmaceutical preparation in an amount effective to reduce platelet count. In important embodiments of the invention, the pharmaceutical preparation comprises the agent in an amount effective to reduce platelet count to low normal levels or to below normal levels.

In yet a further aspect, the invention provides a sustained release device that comprises an agent that reduces platelet count in a subject, wherein the agent is released for at least 7 days. In one embodiment, the sustained release device further comprises a an agent for treating vascular disease or vascular complications. The an agent for treating vascular disease or vascular complications may be an anti-thrombotic agent but is not so limited. In one embodiment, the anti-thrombotic is selected from the group consisting of an anti-coagulant agent, a fibrinolytic agent and an inhibitor of platelet function.

Preferably, the agent is released from the sustained release device in an amount effective to reduce platelet count in a subject to low normal or below normal levels.

In another aspect, a subject's blood is treated extracorporeally to reduce platelet count to below normal levels using procedures such as by pheresis or adsorption of platelets and removal. Subjects, target platelet count and concurrent therapies are as described above. This aspect of the invention is particularly suited to acute therapy, although it is not so limited.

In still another aspect the invention provides a method for treating a subject having above normal platelet count comprising administering to the subject in need of such treatment an MPL pathway inhibitory agent in an amount effective to reduce platelet count.

DETAILED DESCRIPTION OF THE INVENTION

Unexpectedly, the invention involves the discovery that treating human subjects, especially those who do not have a hematological proliferative disorder, to induce a lower platelet count (such as to low normal levels or in some preferred instances to below normal levels) can have desirable medical benefit without significant adverse side effects.

The invention is premised in part on the discovery that a reduction in platelet count in a subject, such as for example to low normal and more preferably below normal levels, reduces the risk of a vaso-occlusive event such as a thrombotic event in the subject without significant adverse side effects. As used herein, a vaso-occlusive event is a event that is characterized by or results in a decrease in the internal diameter of blood vessels either locally or systemically to an extent which impedes blood flow in a subject and which for the purposes of the invention is of a pathological nature. Thus, a vaso-occlusive event embraces pathological narrowing or occlusion of a stent, a vascular graft or a blood vessel. As used herein, "pathological narrowing or occlusion" refers to narrowing or occlusion which is abnormal and/or disease-related. A vaso-occlusive event includes events which cause blood vessel narrowing or occlusion (such as thrombotic events, thromboemobolic events and intimal hyperplasia) as well as conditions which result from such blood vessel narrowing (such as myocardial infarction and ischemic stroke).

A thrombotic event is an event associated with the formation or presence of a thrombus in a subject, particularly when present in the vasculature. A thrombus is an aggregation of blood factors, primarily platelets and fibrin with entrapment of cellular elements, frequently causing vascular obstruction at the point of its formation. Thrombotic events embrace thrombosis at a primary site as well as at a distal site (i.e., thromboembolism). Thrombosis collectively refers to diseases caused by the formation, development, or presence of a thrombus. Thromboembolism refers to diseases characterized by the blocking of a vessel, other than at the initial site of thrombus formation, by a thrombus which has been carried to the distal site by the blood current. As used herein, the term thrombosis is intended to embrace thromboembolism.

Thrombotic events including thromboembolic events can be serious medical conditions particularly since they can cause a reduction in blood flow to critical organs including the brain and myocardium. Examples of thrombotic events include but are not limited to arterial thrombosis, including stent and graft thrombosis, cardiac thrombosis, coronary thrombosis, heart valve thrombosis and venous thrombosis. Cardiac thrombosis is thrombosis in the heart. Arterial thrombosis is thrombosis in an artery. Coronary thrombosis is the development of an obstructive thrombus in a coronary artery, often causing sudden death or a myocardial infarction. Venous thrombosis is thrombosis in a vein. Heart valve thrombosis is a thrombosis on a heart valve. Stent thrombosis is thrombosis resulting from and/or located in the vicinity of a vascular stent. Graft thrombosis is thrombosis resulting from and/or located in the vicinity of an implanted graft, particularly a vascular graft.

Examples of conditions or disorders that result from thrombotic events include but are not limited to myocardial infarction, stroke, transient ischemic attacks, amaurosis fugax, aortic stenosis, cardiac stenosis, coronary stenosis and pulmonary stenosis. Stenosis is the narrowing or stricture of a duct or canal. Coronary stenosis is the narrowing or stricture of a coronary artery. Cardiac stenosis is a narrowing or diminution of any heart passage or cavity. Pulmonary stenosis is the narrowing of the opening between the pulmonary artery and the right ventricle. Aortic stenosis is narrowing of the aortic orifice of the heart or of the aorta itself.

Vaso-occlusive events also include disorders in which the blood vessel narrowing results not necessarily from a thrombus but rather a thickening of the vessel wall such as with intimal hyperplasia. Intimal hyperplasia refers to a condition characterized by abnormal proliferation of the cells of the intimal layer of the blood vessel wall.

Thus, one aspect of the invention relates to a method for reducing the risk of a thrombotic event. In a particular embodiment, the method reduces the risk of stroke. Stroke is a condition resulting from the lack of oxygen to the brain, resulting from one or more occlusive thrombi. Depending on the area of the brain affected, stroke can result in a wide range of symptoms from transient ischemic attacks to death (e.g., coma, reversible or irreversible paralysis, speech problems or dementia). In preferred embodiments, the stroke is non-hemorrhagic in nature.

The method of the invention in another embodiment relates to reducing the risk of myocardial infarction. Myocardial infarction refers to an irreversible injury to the heart muscle. Myocardial infarction generally results from an abrupt decrease in coronary blood flow following a thrombotic occlusion (e.g., a thromboembolism) of a coronary artery. The thrombus, in many instances, forms after the rupture of atherosclerotic plaques in diseased coronary arteries. Such injury is highly correlated with factors such as cigarette smoking, hypertension and lipid accumulation.

Transient ischemic attack is a transient acute neurological dysfunction resulting from a thromboembolism in the cerebral circulation. Amaurosis fugax is the temporary monocular blindness resulting from a thromboembolism in the retinal vasculature.

The methods of the invention can be used either prophylactically to reduce the risk of a primary or a secondary vaso-occlusive event such as a thrombotic event or therapeutically to treat such an event. A primary vaso-occlusive event refers to the first known vaso-occlusive event experienced by the subject. A secondary vaso-occlusive event refers to a vaso-occlusive event which occurs in a subject known or diagnosed as having previously experienced a vaso-occlusive event (i.e., a primary vaso-occlusive event).

According to the invention, the risk of a vaso-occlusive event such as a thrombotic event is reduced by administering to a subject an agent that reduces platelet count to a low normal and more preferably a below normal level. The preferred agent is all aspects and embodiments of the invention is a MPL pathway inhibitory agent. A "normal" platelet count as used herein may be a level in a control population, which preferably includes subjects having similar characteristics as the treated individual, such as age and sex. The "normal" level can also be a range, for example, where a population is used to obtain a baseline range for a particular group into which the subject falls. Thus, the "normal" value can depend upon a particular population selected. Preferably, the normal levels are those of apparently healthy subjects who have no prior history of platelet-mediated disorders. Such "normal" levels, then can be established as preselected values, taking into account the category in which an individual falls. Appropriate ranges and categories can be selected with no more than routine experimentation by those of ordinary skill in the art. Either the mean or another preselected number within the range can be established as the normal preselected value.

As used herein, the terms "platelet level", "platelet number" and "platelet count" are used interchangeably to refer to the number of platelets per a given volume of blood in a subject. The platelet count may be referred to in a number of ways (e.g., per $\mu l$ of blood, per ml of blood, etc.). Generally, platelet counts are referred to herein as the number of platelets per $\mu l$ of blood (i.e., platelets per $\mu l$), however other units may be used.

According to the invention, the risk of a vaso-occlusive event such as a thrombotic event is reduced by administering to a subject an agent that reduces platelet count to a "low normal level" and in some embodiments to a "below normal level". A "normal" platelet count as used herein may be a level in a control population, which preferably includes subjects having similar characteristics as the treated individual, such as age and sex. The "normal" level can also be a range, for example, where a population is used to obtain a baseline range for a particular group into which the subject falls. Thus, the "normal" value can depend upon a particular population selected. Preferably, the normal levels are those of apparently healthy subjects who have no prior history of platelet-mediated disorders. Such "normal" levels, then can be established as preselected values, taking into account the category in which an individual falls. Appropriate ranges and categories can be selected with no more than routine experimentation by those of ordinary skill in the art. Either the mean or another preselected number within the range can be established as the normal preselected value.

As used herein, the terms "platelet level", "platelet number" and "platelet count" are used interchangeably to refer to the number of platelets per a given volume of blood in a subject. The platelet count may be referred to in a number of ways (e.g., per $\mu l$ of blood, per ml of blood, etc.). Generally, platelet counts are referred to herein as the number of platelets per $\mu l$ of blood (i.e., platelets per $\mu l$), however other units may be used.

As is known in the art, the typical range for platelets in a "healthy" human subject is about $150\times10^3$ to $450\times10^3$ platelets per $\mu l$ of blood (mean $300\times10^3$ platelets per $\mu l$). Thus, "below normal levels" of platelets, as used herein, in this population is typically less than $150\times10^3$ platelets/$\mu l$. "Low normal levels" as used herein refer to a platelet count which is 10% less than the mean normal platelet count. Thus, for the population just mentioned, low normal levels would be $270\times10^3$ platelets/$\mu l$. Human subjects who have a platelet count of less than $100\times10^3$ platelets/$\mu l$ are considered thrombocytopenic. Platelet counts of less than $25\times10^3$ platelets/$\mu l$ indicate severe thrombocytopenia. The invention intends to embrace reductions in platelet counts resulting in platelet counts of equal to or less than $270\times10^3$, $260\times10^3$, $250\times10^3$, $240\times10^3$, $230\times10^3$, $220\times10^3$, $210\times10^3$ platelets/$\mu l$ of blood. In preferred embodiments the platelet counts are equal to or less than $200\times10^3$, $190\times10^3$, $180\times10^3$, $170\times10^3$, $160\times10^3$, $150\times10^3$, $140\times10^3$, $130\times10^3$, $120\times10^3$, $110\times10^3$, $100\times10^3$ platelets/$\mu l$, above the level that is considered thrombocytopenic. Nonetheless, it will be understood that it may be desirable depending on factors such as the particular disease, and the age, physical condition of the subject that lower levels are desirable, such as platelet counts equal to or less than $90\times10^3$, $80\times10^3$, $70\times10^3$, $60\times10^3$, $50\times10^3$, and $25\times10^3$ platelets/$\mu l$ of blood. In preferred embodiments, platelet count is reduced to below $200\times10^3$ platelets/$\mu l$ in a human subject. In more preferred embodiments, the platelet count is reduced to below $150\times10^3$ platelets/$\mu l$ while in some other even more preferred embodiments the platelet count is reduced to below $100\times10^3$ platelets/$\mu l$ in a human subject.

In some instances, it may be desirable to treat subjects having a platelet count in the normal range in order to reduce their platelet count and thereby reduce the risk of a vaso-occlusive event even if the post-treatment platelet count is still in the normal range. As an example, the methods of the invention may be used to treat a subject who has a platelet count of $450\times10^3$ platelets/$\mu l$ which while high, is still in the normal range. The subject may be treated in order to reduce the platelet count to either a lower level within the normal range (e.g., a low normal level, as described herein) or to a below normal level.

Platelet reductions may also be measured as a percentage of the pre-treatment platelet count in a subject. Thus the agents of the invention may be administered in an amount effective to reduce platelet count by at least 5% to at least 95% of pre-treatment levels. In some embodiments, the agents are administered in an amount effective to reduce platelet count by at least 10%, at least 20%, at least 30%, at least 40%, at least 50%, at least 60%, at least 70%, at least 80%, or at least 90% of pre-treatment levels. In some embodiments, the subjects are normal subjects who do not have an abnormally high level of circulating platelets such as a platelet count greater than $500\times10^3$ platelets per $\mu l$, or greater than $600\times10^3$ platelets per $\mu l$ which may be due to a hematological proliferative disorder. However, in other embodiments the subjects are normal subjects who have a high level of circulating platelets which is still however within the normal range. The invention intends to treat this latter group of subjects provided the subject does not have a hematological proliferative disorder such as myeloproliferative disease. In preferred embodiments, platelets are reduced by at least 20% of pre-treatment levels. In more preferred embodiments, platelets are reduced by at least 20% to at least 90% of pre-treatment levels. In still other embodiments, platelets are reduced by over 50% of pre-treatment levels.

The subjects may be treated so as to achieve both a drop in platelet count below an absolute level (such as for example below $200\times10^3$ platelets per $\mu l$) and a particular percentage drop in platelet count relative to pre-treatment levels (such as for example at least 10%). As an example, a subject may be treated so as to reduce platelet count by at lest 20% and to achieve a platelet count of less than $200\times10^3$ platelets per $\mu l$.

The invention intends to treat subjects who would benefit from inhibiting the growth of an existing thrombus or lowering of the risk of a vaso-occlusive event such as a thrombotic event.

A subject is a mammal including humans, nonhuman primates, dogs, cats, sheep, goats, horses, cows, pigs or rodents. The preferred subject is a human. The subject may be apparently healthy. An apparently healthy subject is one who, at the time of treatment, does not exhibit disease symptoms. In other words, such individuals, if examined by a medical professional, would be characterized as healthy and free of symptoms of disease. The apparently healthy subjects however may still demonstrate particular risk factors which may place them at an elevated risk of a thrombotic event. For example, such subjects may be apparently healthy and still have a family history of thrombosis-related disorders. Alternatively, the subject may have symptoms of vaso-occlusive disease (such as chest pain, heart palpitations, shortness or breath, as well as a wide range of other symptoms well known to a medical practitioner of ordinary skill) or may have been diagnosed with such disease.

In still other embodiments the subject is one who is otherwise free of symptoms calling for treatment with an agent that reduces platelet count in the subject. These subjects may not necessarily be apparently healthy but at a minimum they do not exhibit symptoms which ordinarily call for treatment specifically with an agent which reduces platelet count. Agents which reduce platelet counts have previously been used to treat some forms of hematological proliferative disorders, particularly those that are characterized by abnormally high platelet counts such as essential thrombocytosis. The hallmark symptom of ET is an abnormally high level of platelets in the circulation, averaging about $600\times10^3$ platelets per $\mu l$ of blood. Involvement and expansion of other hemopoietic cell types is not necessarily a common feature of ET. Splenomegaly may also be observed in such patients. Secondary thrombocytosis is another disease state associated with an abnormally elevated number of platelets. This latter condition is distinguished from ET in that it results from a variety of primary conditions such as recovery from acute infection, malignant diseases including carcinoma and lymphoma, hemolytic anemia, acute hemorrhage, iron deficiency, response to certain drugs and chronic inflammatory disorders. Subjects for whom the methods of the invention are not intended are those diagnosed with conditions which already call for treatment with an agent that reduces platelet count, i.e., secondary thrombocytosis, essential thrombocytosis, polycythemia vera, chronic myelogenous leukemia and myelofibrosis. In other words, in some preferred embodiments, the subject is not one who has, or who has been diagnosed with, a hematological proliferative disorder (such as myeloproliferative disease) which indicates the need for platelet lowering therapy.

The subject can also be one who is at abnormally elevated risk of a thrombotic event. The subject to be treated may be one who is prone to a thrombotic event. Included in this category of subjects are (1) those who have undergone a surgical procedure and are immobilized following such a procedure, (2) those who have chronic congestive heart failure, (3) those who have atherosclerotic vascular disease, (4) those who have malignancy preferably other than a hematological malignancy which results in abnormally high platelet counts, and (5) those who are pregnant. A large majority of human subjects prone to thrombotic events do not manifest any observable perturbation in hemostasis.

One category of subjects with an abnormally elevated risk of a thrombotic event is those subjects who have previously experienced a primary thrombotic event. Subjects having an abnormally elevated risk of a thrombotic event also include (i) those who have inherited a disposition towards thrombosis, for example those with a family history of thrombosis related disorders, (ii) those who have acquired a risk of a thrombotic event such as surgical patients, and (iii) those who engage in lifestyle habits which are considered high risk indicators for thrombosis.

One category of subjects with an abnormally elevated risk of thrombosis is those subjects having vascular disease. Vascular disease is a term which broadly encompasses all disorders of blood vessels (collectively known as the vasculature) including small and large arteries and veins, and blood flow. The most prevalent form of vascular disease is arteriosclerosis, a condition associated with the thickening and hardening of the arterial wall. Arteriosclerosis or an arteriosclerotic condition as used herein means classical atherosclerosis, accelerated atherosclerosis, atherosclerosis lesions and any other arteriosclerotic conditions characterized by undesirable endothelial and/or vascular smooth muscle cell proliferation, including vascular complications of diabetes. It is believed to be responsible for the majority of deaths in the United States and in most westernized societies.

Arteriosclerosis of the large vessels is referred to as atherosclerosis. Atherosclerosis is the predominant underlying factor in disorders such as coronary artery disease, aortic aneurysm, arterial disease of the lower extremities and cerebrovascular disease. Other types of arteriosclerosis include focal calcific arteriosclerosis (Monckeberg's sclerosis) and arteriolosclerosis. Arterial diseases other than arteriosclerosis include congenital structural defects, inflammatory or granulomatous diseases (e.g., syphilitic aortitis), and small vessel disorders such as hypertension and autoimmune diseases. Disorders which are associated with early arteriosclerosis include diabetes mellitus, hypertension, familial hypercholesterolemia, familial combined hyperlipidemia, familial dysbetalipoproteinemia, familial hypoalphalipoproteinemia, hypothyroidism, cholesterol ester storage disease, systemic lupus erythrematosus, homocysteinemia, chronic renal insufficiency, chronic vitamin D intoxication, pseudoxanthoma elasticum, idiopathic arterial calcification in infancy, aortic valvular calcification in the elderly and Werner's syndrome.

Subjects with cardiovascular disease, cerebrovascular disease and/or peripheral vascular disease (e.g., diabetic feet, failed grafts) are also considered at abnormally high risk of a thrombotic event. Cardiovascular disease refers to a number of disorders of the heart and vascular system. Cerebrovascular disease refers to a number of disorders of the blood vessels in the cerebrum or the brain. Peripheral vascular disease is disorder of the peripheral vasculature including that of the lower extremities.

The method of the invention can be used to treat subjects at abnormally elevated risk of experiencing particular vaso-occlusive events. For example, a subject with an abnormally elevated risk of myocardial infarction can be treated according to the method of the invention. Subjects may be treated prophylactically to reduce the risk of a primary or secondary myocardial infarction. As used herein, subjects having an abnormally elevated risk of myocardial infarction include those with unstable angina, multiple coronary risk factors, and Prinzmetal's variant angina. Less common etiologic factors include hypercoagulability, coronary emboli, collagen vascular disease, and cocaine abuse.

A subject with an abnormally elevated risk of stroke, for example non-hemorrhagic stroke, can also be treated according to the invention. Subjects having an abnormally elevated risk of an ischemic stroke are a category determined according to conventional medical practice; such subjects may also be identified in conventional medical practice as having known risk factors for stroke or having increased risk of cerebrovascular events. The primary risk factors include hypertension, hypercholesterolemia, and smoking. Subjects having an abnormally elevated risk of an ischemic stroke also include individuals having any cardiac condition that may lead to decreased blood flow to the brain, such as atrial fibrillation, ventrical tachycardia, dilated cardiomyopathy and other cardiac conditions requiring anticoagulation. Subjects having an abnormally elevated risk of an ischemic stroke also include individuals having conditions including arteriopathy or brain vasculitis, such as that caused by lupus, congenital diseases of blood vessels, such as cadasil syndrome, or migraine, especially prolonged episodes.

Another category of subjects with an abnormally elevated risk of a thrombotic event are those subjects who will undergo or those who have already undergone a surgical or mechanical interventional procedure for the purposes of vessel repair and/or revascularization. Such procedures may be therapeutic or diagnostic in nature, and thus can also be elective or emergency treatments, and most likely involve the risk of formation of thrombi or the release of emboli. Procedures which fall into this category include but are not limited to vascular surgery including peripheral vascular surgery, vascular grafting, vascular laser therapy, vascular replacement, including prosthetic valve replacement, and vascular stenting, ventricular assist procedures, artificial heart transplant, heart and other organ transplants which require an interfacing of the transplanted organ with the vasculature of the transplant recipient, thrombectomy, coronary angiography, coronary and peripheral stent placements, carotid artery procedures including carotid endarterectomy, brain angiography, neurosurgical procedures in which blood vessels are compressed or occluded, cardiac catheterization, vascular angioplasty, including balloon angioplasty, coronary by-pass surgery. In addition to the risk of thrombus formation during or immediately following the surgical procedure, there also exists a risk to subjects who have undergone a surgical procedure and are currently immobilized following the procedure. Thus the invention seeks to embrace treatment of the subject prior to, during and following surgical procedures.

Other factors which predispose subjects to abnormally elevated risk of a thrombotic event are genetic risk factors and lifestyle habits. Inherited conditions can generally be regarded as hypercoaguable states or pre-thrombotic states. The pre-thrombotic subject can sometimes be identified if they present with a personal history of early (i.e., adolescent or as a young adult) and/or repeated thromboembolic events in the absence of an overt pre-disposing condition, and/or a family history of thrombosis related conditions. Subjects who have experienced pain in walking, ischemia (i.e., a deficiency of blood flow to an area of the body due to functional constriction or obstruction of a blood vessel), gangrene (i.e., a death of tissue, usually considerable in mass and generally associated with loss of blood flow) and chest pain, may be regarded as having a personal history of arterial thrombosis or stroke, and are thus also at risk of a thrombotic event. Risk factors for a thrombotic event also include inheritable hematological abnormalities such as deficiency and/or dysfunction in any number of factors including anti-thrombin III, protein C, protein S and clotting factor V. Cardiovascular abnormalities, i.e., congenital structural abnormalities of the cardiovascular system, are also considered risk factors for thrombotic events. Vascular abnormalities such as atherosclerotic plaque ruptures are also considered a risk factor.

Lifestyle risk factors include smoking, failure to exercise and diet to the extent that it affects other risk factors such as obesity, high cholesterol, hyperlipidemia and high blood pressure (i.e., hypertension). High cholesterol (i.e., hypercholesterolemia), high blood pressure (i.e., hypertension), hyperlipidemia, and obesity are most certainly also induced by a variety of non-dietary causative elements including genetic and environmental factors.

A hyperlipidemic subject is defined as one whose cholesterol and triglyceride levels equal or exceed the limits set as described herein for both the hypercholesterolemic and hypertriglyceridemic subjects. A hypercholesterolemic subject (i.e., one with high cholesterol) has either an LDL (i.e., low-density lipoprotein) level of >160 mg/dL, or an LDL level of >130 mg/dL and at least two risk factors selected from the group consisting of male gender, family history of premature coronary heart disease, cigarette smoking (more than 10 cigarettes per day), hypertension, low HDL (<35 mg/dL), diabetes mellitus, hyperinsulinemia, abdominal obesity, high lipoprotein (a), and a personal history of cerebrovascular disease or occlusive peripheral vascular disease. A hypertriglyceridemic subject has a triglyceride (TG) level of >250 mg/dL.

Subjects who are hypertensive (i.e., those that have high blood pressure) are also at risk of a thrombotic event. A hypertensive subject is one who experiences persistently high arterial blood pressure. Hypertension may have no known cause, in which case it is referred to as essential or idiopathic hypertension. Alternatively, hypertension may be associated with other primary diseases, in which case it is referred to as secondary hypertension. It is generally considered a risk factor for the development of heart disease, peripheral vascular disease, stroke and kidney disease. In adults, a diastolic pressure below 85 mmHg is considered normal, between 85 and 89 mmHg is considered high normal, 90 to 104 mmHg is considered mild hypertension, 105–114 mmHg is considered moderate hypertension and 115 mmHg or greater is considered severe hypertension. When the diastolic pressure is below 90 mmHg, a systolic pressure below 140 mmHg indicates normal blood pressure, between 140 and 159 mmHg is borderline isolated systolic hypertension and 160 mmHg or higher is isolated systolic hypertension. Thus, generally, normal subjects are those with a blood pressure of 140/90 or less.

Other risk factors which contribute to an elevated risk of thrombotic events, and the disorders which underlie such thrombotic events (e.g., arteriosclerosis), include hyperlipidemia, hyperglycemia and diabetes mellitus, stress and personality, low index of high density lipoproteins (HDL), male gender, age, hyperinsulinemia, high lipoprotein (a) and a personal history of cerebrovascular disease or occlusive peripheral vascular disease. Hyperglycemia is a condition associated with too high a level of glucose in the blood, sometimes indicative of uncontrolled diabetes. It occurs when the body does not have enough insulin or cannot effectively use insulin to metabolize glucose. This condition may be associated with diabetes mellitus, Cushing's disease, and Cushing's syndrome. Signs of hyperglycemia are significant thirst, dry mouth, and frequent urination. Normal asymptomatic human subjects who are at least 50 years of age, and more preferably 60 years of age, are also at increased risk for thrombosis.

Subjects at risk of having intimal hyperplasia as well as those having intimal hyperplasia are also intended to be treated according to the methods of the invention. Thus, the method of the invention can be used to treat subject who have or at risk of having intimal hyperplasia, as well as to reduce the risk of intimal hyperplasia. One common form of intimal hyperplasia is atherosclerosis.

The invention also intends to treat, in other aspects, subjects who have had a primary vaso-occlusive event or who are currently experiencing a vaso-occlusive event, including subjects who have been diagnosed with thrombosis or as having a thrombotic event. The invention can also be used to treat subjects that have manifest an abnormal healing of blood vessels.

The treatment method of the invention involves the administration to a subject of an agent that reduces circulating platelet count in the subject. Agents which reduce platelet count are herein sometimes referred to as platelet reducing agents. Preferably such agents have the specific effect of reducing only platelet count without affecting levels of other cell types, although it should be understood that an agent may also reduce levels of other cell types provided these latter reductions do not induce unacceptable levels of adverse side effects associated with such reduction in other cell types. For example, the agent may reduce levels of megakaryocytes, the precursors of platelets, and such reduction should not have any undesirable side effect. As another example, an agent may be cytotoxic for a megakaryocyte lineage restricted cell, such as a platelet, and another blood cell, or a common precursor of these two cell types, in which case the agent is acceptable only if platelet count can be reduced to below normal levels without unacceptable levels of side effects associated with such reduction in the other cell type. In still another example, the agent may inhibit megakaryocyte function. It will be apparent to persons of ordinary skill in the art how to select and distinguish between such agents.

In one preferred embodiment, the agent is an MPL pathway inhibitory agent. An MPL pathway inhibitory agent is an agent that interferes with the MPL pathway. The MPL pathway is the set of events which start when a MPL ligand binds to a MPL receptor and which result in an increase in platelet count and platelet maturation. The pathway includes ligand-receptor binding, intracellular signaling events, and modulation of gene expression. A MPL pathway inhibitory agent may be an agent that binds to MPL ligand and thereby interferes with the ability of MPL ligand to bind MPL receptor, or an agent that binds to MPL receptor and thereby interferes with the ability of MPL receptor to bind to MPL ligand or interferes with the ability of MPL receptor to transduce a signal to another molecule in the MPL pathway, or an agent that binds to an intracellular cell signaling compound that relays a signal from the MPL receptor, but is not so limited. In important embodiments, the agent is one which binds to an MPL receptor or one which binds to a thrombopoietin molecule.

Agents already known to reduce platelet count include but are not limited to (1) cAMP phosphodiesterase inhibitors (e.g., anagrelide), 6,7-dichloro-1,5-dihydroimidazo-[2,1-b] quinazolin-2(3H)-one or 6,7-dichloro-1,2,3,5-tetrahydroimidazo[2,1-b]quinazolin-2-one (U.S. Pat. Nos. 3,932,407; 4,146,718; RE31,617, Haematologica 1992 77:40–3), (2) antibodies to cell surface receptors specifically expressed by platelets or megakaryocytes such as glycoprotein IIb/IIIa receptor antibodies, (3) most chemotherapeutic anti-cancer drugs such as busulphan (Br. J. Haematol. 1986 62:229–37), hydroxyurea (N Engl J Med 1995 332:1132–6), hepsulfan, phosphorus-32 (Br J Radiol 1997 70:1169–73), pipobroman (Scand J. Haematol 1986 37:306–9), cyclophosphamide (J Cell Physiol 1982 112:222–8), certain alkylating agents and certain antimetabolites, (4) cytokines, growth factors and interleukins such as alpha-interferon (Cancer Immunol Immunother 1987 25:266–73), gamma-interferon, transforming growth factor-beta, neutrophil activating peptide-2 and its analogs (U.S Pat. No. 5,472,944), macrophage inflammatory protein and its analogs (U.S. Pat. No. 5,306,709), (5) compounds secreted by either platelets or megakaryocytes such as platelet-factor 4 (U.S. Pat. No. 5,185,323), transforming growth factor-beta, the 12–17 kD glycoprotein produced by megakaryocytes, thrombin and thrombospondin and its amino (1–174 amino acid) terminal fragment (J Lab Clin Med 1997 129:231–8), and (6) other agents including anti-cheloid agents such as Tranilast (Rizaben) (J Dermatol 1998 25:706–9); forskolin and spleen anti-maturation factor (U.S. Pat. No. 4,088,753).

All the afore-mentioned agents may be suitable for use in the method of the invention to reduce normal platelet count in a subject preferably to a below normal level with the purpose of preventing or treating a vaso-occlusive event such as a thrombosis. In some instances these benefits are achieved by reducing the platelet count to low normal while in other more preferred instances the platelet count is reduced to below normal levels. It should be understood that the agents useful in the invention may still be capable of affecting platelet function as well as reducing platelet count. However, in some embodiment, such agents are used in a dose, formulation and administration schedule which favor the platelet count reducing activity of the agent and do not impact significantly, if at all, on platelet function.

Many of the above-listed agents while capable of reducing platelet count can also impact upon other cell lineages, particularly other hemopoietic cell lineages. It is preferred that the agents used in the methods of the invention are provided or administered in a manner which limits effects on other cell types. One way this can be accomplished is to identify agents which while perhaps not exclusive for the megakaryocyte lineage, have limited specificity for other cell lineages. Most of the agents listed above fall into this category. Another way of limiting unnecessary side effects is to administer the agent in the maximal dose which reduces platelet count and which does not impact upon other cell types. Such determination can be made using in vitro clonogenic assays such as those described herein, which are standard in the art. Yet another way of providing specificity is to conjugate an otherwise non-specific agent with a molecule which will target the non-specific agent to megakaryocyte and platelets. Potential targeting molecules are those which normally bind receptors uniquely expressed on cells of the megakaryocyte lineage.

Yet another way of ensuring specificity for the megakaryocytes and platelets is to interfere with molecules reported to be uniquely expressed by these cell types and which are involved in the development, differentiation and proliferation of these cell types. Proteins and peptides known to be specific for platelet production and/or megakaryocyte growth and development include MPL receptor and, its ligand, thrombopoietin and the transcription factor NF-E2. MPL receptor is a cell surface tyrosine kinase protein expressed almost exclusively by platelets and their precursors, megakaryocytes. Agents which interfere with the normal interactions of these proteins and/or the signaling pathways in which they are involved are also considered suitable for use in the methods of the invention, provided they reduce platelet count without significant adverse side effects.

Agents which interfere with cell surface interactions, signaling pathways and transcriptional events required for development, differentiation and proliferation of megakaryocyte lineage are embraced by the invention. Agents which interfere with any of the afore-mentioned interactions and pathways can do so in a number of ways. For example, one class of agents may bind to the extracellular domain of MPL receptor, and thereby prevent binding of thrombopoietin to the receptor. Agents with this property may bind directly to one or more residues required for thrombopoietin binding to the MPL receptor. Alternatively, the agent may bind to a completely distinct region of the MPL receptor and thereby induce a conformational change in the MPL receptor that alters the native thrombopoietin binding site to the extent that such native ligand binding is precluded or at the very least reduced. Other useful agents may induce conformational changes within MPL receptor which alter the kinase domain and/or the phosphorylation site of MPL receptor. Agents which induce conformational changes in MPL receptor may bind to either the extracellular or the intracellular domain of MPL receptor.

Antisense molecules are also useful as MPL pathway inhibitory agents. As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness. The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose.

Still other agents embraced by the invention are those which bind to thrombopoietin and preclude or limit its ability to associate with MPL receptor. These latter agents may bind thrombopoietin at the site at which the ligand normally binds to the receptor or at an overlapping site. Alternatively, they may bind at a distal site but induce a conformational change in the thrombopoietin molecule which alters its MPL receptor binding site.

Other useful agents prevent signal transduction from the MPL receptor to cytoplasmic signaling molecules, possibly by masking the kinase domain or the phosphorylation site of the MPL receptor. Agents which mask the kinase domain or the phosphorylation sites on intracellular substrates of MPL receptor are also useful in the invention. Masking of kinase domains or phosphorylation sites can be accomplished by binding of the agent. Drachman and Kaushansky have identified the residues in the MPL cytoplasmic domain which are phosphorylated and those involved in signal transduction. (Proc Natl Acad Sci USA 1997 94:2350–5) Similarly, Morita et al. have performed a mutational analysis of the intracellular domain of MPL receptor and identified domains involved in and essential for signal propagation to other cytoplasmic proteins. (Morita et al, FEBS Lett 1996 395:228–34) With this information, agents which bind to the critical regions identified by Morita et al. would be useful in the methods described herein.

Cell signaling mediators involved in the thrombopoietin-MPL receptor pathway include the tyrosine kinases JAK2, Shc, STAT3, STAT5, Vav, Crk-1 and Tec, among others. Although none of these signal mediators has been reported to be inherently unique for the MPL-thrombopoietin pathway, inhibition of these signaling molecules may still be effected specifically in platelets and their megakaryocyte precursors. Such targeting may involve conjugation of signaling inhibitors, such as kinase inhibitors, to a target molecule specific for the megakaryocyte lineage. As an example, conjugation of an inhibitor to a thrombopoietin molecule would serve to deliver the inhibitor only to cells expressing MPL receptor, the overwhelming majority of which are megakaryocyte lineage cells. Kinase inhibitors have been reported in the prior art and would be known to the ordinary artisan. One example of such an inhibitor is the compound AG-490 which inhibits JAK kinase. This inhibitor has been reported to inhibit proliferation of a megakaryocyte cell line in vitro. Specific targeting of this inhibitor, and others like it, to cells of the megakaryocyte/platelet lineage through conjugation with lineage specific ligands or antibodies is thus also embraced by the invention.

One preferred agent is an MPL receptor antagonist. Antagonists are generally described as compounds which tend to nullify the action of another, such as a drug that binds to a cell receptor without eliciting a biological response.

Agonists, on the other hand, are compounds which have an affinity for and ability to stimulate a physiological activity of cell receptors normally stimulated by a naturally occurring substance, and are thereby capable of triggering a biochemical response. Agonists of the thrombopoietin-MPL receptor pathway have been identified. U.S. Pat. No. 5,756,083 discloses the production of MPL ligand (i.e., thrombopoietin) analogs which encompass changes to glycosylation sites relative to the native ligand.

Knowledge of the native ligand of MPL receptor (i.e., thrombopoietin) as well as the identification of several agonists of MPL receptor facilitate a rational design of putative MPL antagonists. Recent studies into the biological activity of thrombopoietin have reported that the amino terminal domain of thrombopoietin is essential for its activity. Specifically it was reported that an Arg-Arg motif located in this domain is critical as is a cysteine residue located two amino acids away from the Arg-Arg motif. (Wada et al. Biochem. Biophys. Res. Commun. 1995 213:1091–8) Thus a library may be synthesized based on a peptide comprising the amino terminal of thrombopoietin in which one or both of the arginine residues and/or the proximal cysteine residue are mutated.

The size of the peptide fragments present in the library will depend upon the nature of the interaction between thrombopoietin and MPL receptor. Reported known agonists to MPL receptor are small peptides, on the order of 15 amino acid residues in length. Thus, antagonist libraries could have the constraint imposed upon them of yielding peptides equal to 15 amino acids in length. Alternatively, given that the activity of thrombopoietin has reportedly been ascribed to a Arg-Arg dipeptide, it may also be desirable to synthesize libraries composed of dipeptides. To this end, Brown et al. (U.S. Pat. No. 5,741,713), the entire contents of which are incorporated herein by reference, disclose methods for producing combinatorial libraries of labeled dipeptides.

As stated above, in the rational design of MPL antagonists, peptide and peptidomimetic libraries can be modeled either as variants of thrombopoietin, the natural ligand of MPL, or as variants of known agonists. As used herein, a "variant" is a polypeptide which contains one or more modifications to the primary amino acid sequence of a known naturally occurring ligand or a synthetically produced agonist.

Rational design of thrombopoietin variants can also be accomplished by comparing and contrasting the amino terminal domains of thrombopoietin, erythropoietin and alphainterferon. The amino terminal domain of thrombopoietin has been reported to be essential for its activity. It has also been reported that the amino terminal domains of thrombopoietin, erythropoietin and alpha-interferon share considerable homology. Alpha-interferon however, unlike thrombopoietin and, to a lesser extent, erythropoietin, does not stimulate megakaryocytes but rather inhibits their proliferation. Thus, a study of the amino acid sequence of this domain of alpha-interferon as well as a structural analysis of this domain and subsequent comparison with thrombopoietin and erythropoietin should elucidate the amino acid residues and three-dimensional conformation involved in the inhibition function. Random or directed mutation of the putative amino acid residues involved in the recognition and/or binding of thrombopoietin to its receptor can identify antagonists of MPL receptor, as described herein.

Antagonists of MPL receptor can be synthesized from peptides or other biomolecules including but not limited to saccharides, fatty acids, sterols, isoprenoids, purines, pyrimidines, derivatives or structural analogs of the above, or combinations thereof and the like. Phage display libraries and chemical combinatorial libraries can be used to develop and select synthetic compounds which are MPL receptor antagonists. Also envisioned in the invention is the use of antagonists made from peptoids, random bio-oligomers (U.S. Pat. No. 5,650,489), benzodiazepines, diversomeres such as dydantoins, benzodiazepines and dipeptides, nonpeptidal peptidomimetics with a beta-D-glucose scaffolding, oligocarbamates or peptidyl phosphonates.

Many if not all of these compounds can be synthesized using recombinant or chemical library approaches. A vast array of candidate antagonists can be generated from libraries of synthetic or natural compounds. Libraries of natural compounds in the form of bacterial, fungal, plant and animal extracts are available or can readily produced. Natural and synthetically produced libraries and compounds can be readily modified through conventional chemical, physical, and biochemical means. Known binding partners of MPL receptor such as thrombopoietin or recently identified MPL agonists may be subjected to directed or random chemical modifications such as acylation, alkylation, esterification, amidification, etc. to produce structural analogs of these binding partners, which may function as antagonists. U.S. Pat. No. 5,830,647 discloses the synthesis of thrombopoietin variants using a variety of techniques including alanine scanning mutagenesis as well as covalent modifications of thrombopoietin. Using techniques similar to those of this latter reference, and coupling them with screens for antagonist activity, it should be possible to identify MPL receptor antagonists. Similarly the techniques utilized by Elliot and disclosed in U.S. Pat. No. 5,756,083, to generate thrombopoietin analogs are also conducive to the identification of MPL antagonists provided these molecules are screened appropriately.

The methods of the invention utilize this library technology to identify small molecules including small peptides which bind to receptor ligand binding sites. One advantage of using libraries for antagonist identification is the facile manipulation of millions of different putative candidates of small size in small reaction volumes (i.e., in synthesis and screening reactions). Another advantage of libraries is the ability to synthesize antagonists which might not otherwise be attainable using naturally occurring sources, particularly in the case of non-peptide moieties.

Synthetic DNA and RNA libraries are also commonly used in the art. For instance, Ellington and Szostak describe the use of random polynucleotide libraries to identify novel ligands (Ellington and Szostak, Nature, 346, 818–822 (1990)). Modifications which create thrombopoietin or MPL antagonist variants can be made at the level of the nucleic acid sequence which encodes thrombopoietin or the agonist. Amino acid substitutions may be made by PCR-directed mutation, site-directed mutagenesis according to the method of Kunkel (Kunkel, Proc. Nat. Acad. Sci. U.S.A. 82: 488–492, 1985), or by chemical synthesis of a nucleic acid molecule encoding thrombopoietin or an agonist.

Methods for preparing libraries of molecules are well known in the art and many libraries are commercially available. Libraries of interest in the invention include peptide libraries, randomized oligonucleotide libraries, synthetic organic combinatorial libraries, and the like. Degenerate peptide libraries can be readily prepared in solution, in immobilized form as bacterial flagella peptide display libraries or as phage display libraries. Peptide ligands can be selected from combinatorial libraries of peptides containing at least one amino acid. Libraries can be synthesized of peptoids and non-peptide synthetic moieties. Such libraries can further be synthesized which contain non-peptide synthetic moieties which are less subject to enzymatic degradation compared to their naturally-occurring counterparts. Libraries are also meant to include for example but are not limited to peptide-on-plasmid libraries, polysome libraries, aptamer libraries, synthetic peptide libraries, synthetic small molecule libraries and chemical libraries. The libraries can also comprise cyclic carbon or heterocyclic structure and/or aromatic or polyaromatic structures substituted with one or more of the above-identified functional groups.

Small molecule combinatorial libraries may also be generated. A combinatorial library of small organic compounds is a collection of closely related analogs that differ from each other in one or more points of diversity and are synthesized by organic techniques using multi-step processes. Combinatorial libraries include a vast number of small organic compounds. One type of combinatorial library is prepared by means of parallel synthesis methods to produce a compound array. A "compound array" as used herein is a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in U.S. Ser. No. 08/177,497, filed Jan. 5, 1994 and its corresponding PCT published patent application W095/18972, published Jul. 13, 1995 and U.S. Pat. No. 5,712,171 granted Jan. 27, 1998 and its corresponding PCT published patent application W096/22529, which are hereby incorporated by reference.

In certain embodiments, the libraries may have at least one constraint imposed upon the displayed peptide sequence. A constraint includes, e.g., a positive or negative charge, hydrophobicity, hydrophilicity, a cleavable bond and the necessary residues surrounding that bond, and combinations thereof. In certain embodiments, more than one constraint is present in each of the peptide sequences of the library.

One of skill in the art will be familiar with methods for predicting the effect on protein conformation of a change in protein sequence, and can thus "design" a variant which functions as an antagonist according to known methods. One example of such a method is described by Dahiyat and Mayo in Science 278:82–87, 1997, which describes the design of proteins de novo. The method can be applied to a known protein to vary only a portion of the polypeptide sequence. By applying the computational methods of Dahiyat and Mayo, specific variants of thrombopoietin or any known MPL agonist confined to regions which bind the receptor ligand binding site can be proposed and tested to determine whether the variant retains a desired conformation. Similarly, Blake (U.S. Pat. No. 5,565,325) teaches the use of known ligand structures to predict and synthesize variants with similar or modified function.

Other methods for preparing or identifying peptides which bind to a particular target are known in the art. Molecular imprinting, for instance, may be used for the de novo construction of macromolecular structures such as peptides which bind to a particular molecule. See, for example, Kenneth J. Shea, Molecular Imprinting of Synthetic Network Polymers: The De Novo synthesis of Macromolecular Binding and Catalytic Sites, TRIP Vol. 2, No. 5, May 1994; Klaus Mosbach, Molecular Imprinting, Trends in Biochem. Sci., 19(9) January 1994; and Wulff, G., in Polymeric Reagents and Catalysts (Ford, W. T., Ed.) ACS Symposium Series No. 308, pp 186–230, American Chemical Society (1986). One method for preparing mimics of thrombopoietin or mimics of MPL receptor agonists involves the steps of: (i) polymerization of functional monomers around a known substrate (the template or in this case, the MPL receptor ligand binding domain) that exhibits a desired activity; (ii) removal of the template molecule; and then (iii) polymerization of a second class of monomers in the void left by the template, to provide a new molecule which exhibits one or more desired properties which are similar to that of the template. In addition to preparing peptides in this manner other binding molecules such as polysaccharides, nucleosides, drugs, nucleoproteins, lipoproteins, carbohydrates, glycoproteins, steroids, lipids, and other biologically active materials can also be prepared. This method is useful for designing a wide variety of biological mimics that are more stable than their natural counterparts, because they are typically prepared by the free radical polymerization of functional monomers, resulting in a compound with a nonbiodegradable backbone. Other methods for designing such molecules include for example drug design based on structure activity relationships which require the synthesis and evaluation of a number of compounds and molecular modeling.

Peptides which bind to the MPL receptor ligand binding site can be generated and identified by conventional screening methods such as phage display procedures (e.g., methods described in Hart, et al., J. Biol. Chem. 269:12468 (1994)). Hart et al. report a filamentous phage display library for identifying novel peptide ligands for mammalian cell receptors. In general, phage display libraries using, e.g., M13 or fd phage, are prepared using conventional procedures such as those described in the foregoing reference. The libraries display inserts containing from 4 to 80 amino acid residues. The inserts optionally represent a completely degenerate or a biased array of peptides. Ligands that bind selectively to a receptor site are obtained by selecting those phages which express on their surface an amino acid sequence which recognizes and binds to the receptor. These phages then are subjected to several cycles of reselection to identify the receptor binding phages that have the most useful binding characteristics. The minimal linear portion of the sequence that binds to the receptor ligand binding site can be determined. Typically, phages that exhibit the best binding characteristics (e.g., highest affinity) are further characterized by nucleic acid analysis to identify the particular amino acid sequences of the peptides expressed on the phage surface and the optimum length of the expressed peptide to achieve optimum binding to the receptor binding site of the ligand or the ligand binding site of the receptor or any other site impacting upon association of the thrombopoietin to MPL receptor.

The displayed peptide sequence can vary in size. As the size increases, the complexity of the library increases. It is preferred that the total size of the displayed peptide sequence (the random amino acids plus any spacer amino acids) should not be greater than about 100 amino acids long, more preferably not greater than about 50 amino acids long, and most preferably not greater than about 25 amino acids long.

A random phage library using filamentous bacteriophage fuse5 has been synthesized for the purpose of identifying peptide agonists of MPL receptor. (Kimura et al. J. Biochem (Tokyo) 1997 122:1046–51) Cwirla et al. were able to identify agonists using recombinant peptide libraries. (Cwirla et al. Science 1997 276:1696–9) The peptide identified by Cwirla et al. has the amino acid sequence Ile-Glu-Gly-Pro-Thr-Leu-Arg-Gln-Trp-Leu-Ala-Ala-Arg-Ala. It is expected that any of these libraries, as well as others like them, would yield MPL receptor antagonists at least with the same frequency and probably with a greater frequency than MPL receptor agonists.

Dower et al. have also reported the synthesis of peptides and compounds that bind to MPL receptor. (U.S. Pat. 5,869,451) Again, peptides and compounds were generated and screened for agonist activity. The approach of Dower et al. can be adopted to synthesize compounds that bind MPL receptor but then further modified to screen for those binding compounds which are capable of antagonist activity using the screening assays described herein.

In yet another approach to the identification of MPL receptor antagonists, antibodies which bind to MPL receptor, and thereby effect their antagonist activity are also embraced by the invention. Antibodies include polyclonal and monoclonal antibodies, prepared according to conventional methodology. Antibodies to MPL can be generated using techniques standard in the art. Deng et al. have described the production of murine monoclonal antibodies specific for MPL receptor by challenging mice with human megakaryocytic cells (Deng et al. Blood 92:1981–8) Thus it is possible to produce murine monoclonal antibodies which specifically bind to MPL receptor through the challenge of mice with cells expressing MPL receptor or perhaps more preferably through challenge with isolated MPL receptor. Of particular importance is the observation by Deng et al. that the murine monoclonal antibody produced, termed BAH-1, functioned as an MPL agonist. It is likely that a similar approach will yield antibodies with antagonistic properties as well. Antibodies generated in such a manner can then be manipulated in a number of ways, as described below. Thus it should be apparent that as yet another approach to generating MPL antagonists, the antibody reported by Deng et al. with MPL agonist properties could be mutagenized to produce an antagonist antibody or antibody fragment.

Significantly, as is well-known in the art, only a small portion of an antibody molecule, the paratope, is involved in the binding of the antibody to its epitope (see, in general, Clark, W. R. (1986) *The Experimental Foundations of Modem Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The putative MPL antagonist compounds so generated can be screened to identify non-naturally occurring putative MPL receptor antagonists. A first set of screens useful in identifying such compounds involve selecting for binding partners of MPL receptor. Compounds such as library members can be screened for their ability to bind to MPL receptor in vitro using standard binding assays well known to the ordinary artisan and described below. For binding to MPL receptor, MPL receptor may be presented in a number of ways including but not limited to cells expressing MPL receptor (such as those described below), an isolated extracellular domain of MPL receptor, a fragment thereof or a fusion protein of the extracellular domain of human thrombopoietin and another protein such as an immunoglobulin. This latter approach was used successfully by Kumura et al. for identification of MPL agonists. (Kimura et al. J. Biochem (Tokyo) 1997 122:1046–51) For some high throughput screening assays the use of purified forms of MPL receptor, its extracellular domain or a fusion of its extracellular domain with another protein may be preferable. Isolation of binding partners may be performed in solution or in solid state according to well-known methods.

In order to increase the specificity of a library for a MPL receptor, the library may be pre-screened by exposing it to a cell population which does not express MPL receptor. In this way, binding partners which are not specific for only MPL receptor can be eliminated or at least reduced in number from the library prior to further screening. Procedures for prescreening include but are not limited to affinity column purification or biopanning.

Standard binding assays are well known in the art, and a number of these are suitable in the present invention including ELISA, competition binding assay (particularly suitable in the present invention since the native substrate of MPL receptor is known), sandwich assays, radioreceptor assays using radioactively labeled thrombopoietin (the binding is blocked in the presence of the antagonist), labeled in vitro protein-protein binding assays, electrophoretic mobility shift assays, immunoassays, cell-based assays such as two- or three-hybrid screens, etc. The nature of the assay is not essential provided it is sufficiently sensitive to detect binding of a small number of library members.

A variety of other reagents also can be included in the binding mixture. These include reagents such as salts, buffers, neutral proteins (e.g., albumin), detergents, etc.

which may be used to facilitate optimal protein-protein. Such a reagent may also reduce non-specific or background interactions of the reaction components. Other reagents that improve the efficiency of the assay may also be used. The mixture of the foregoing assay materials is incubated under conditions under which the MPL receptor normally specifically binds the thrombopoietin. The order of addition of components, incubation temperature, time of incubation, and other perimeters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours. After incubation, the presence or absence of specific binding between the MPL receptor and thrombopoietin or the MPL antagonist is detected by any convenient method available to the user.

Typically, a plurality of assay mixtures are run in parallel with different agent concentrations to obtain a different response to the various concentrations. One of these concentrations serves as a negative control, i.e., at zero concentration of agent or at a concentration of agent below the limits of assay detection.

For cell-free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., columns or gels of polyacrylamide, agarose or sepharose, microtiter plates, microbeads, resin particles, etc. The substrate preferably is chosen to maximum signal to noise ratios, primarily to minimize background binding. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

For cell-free binding assays, one of the components usually comprises, or is coupled to, a detectable label. A wide variety of labels can be used, such as those that provide direct detection (e.g., radioactivity, luminescence, optical or electron density, etc). or indirect detection (e.g., epitope tag such as the FLAG epitope, enzyme tag such as horseradish peroxidase, etc.). The label may be bound to a library member, or incorporated into the structure of the library member. The MPL receptor, thrombopoietin or the antagonist of the invention may be labeled by a variety of means for use in screening. There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the binding partners used in the screening assays, or will be able to ascertain such, using routine experimentation. Furthermore, the coupling of these labels the binding partners used in the screening assays of the invention can be done using standard techniques common to those of ordinary skill in the art.

Another labeling technique which may result in greater sensitivity consists of coupling the binding partners to low molecular weight haptens. These haptens can then be specifically altered by means of a second reaction. For example, it is common to use haptens such as biotin, which reacts with avidin, or dinitrophenol, pyridoxal, or fluorescein, which can react with specific anti-hapten antibodies.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

One example of a suitable binding assay involves the use of an MPL receptor or a MPL receptor fusion protein immobilized on a resin contained within a column. This can be achieved by using a glutathione-S-transferase (GST) fusion of the receptor and a column containing anti-GST antibody. The receptor-GST fusion polypeptide is first immobilized on the column or resin, followed by the addition of a suspension of compounds such as for example library members in a solution compatible with the binding of select compounds to the ligand binding site of the receptor. The column is then washed to remove any residual non-bound compounds. The bound compounds are then eluted by changing the conditions on the column such that binding to the ligand binding site is no longer favored, such as pH or ionic concentration change. The eluate is collected and the compounds contained therein are further analyzed. In the case where the compounds are peptides, the eluted peptides can be sequenced using standard Edman degradation amino acid sequencing techniques or in the case of non-peptide moieties, the eluted compounds are analyzed by standard analytical techniques such as HPLC and mass spectroscopy. Apparati for performing Edman degradation sequencing, an example of which is the Applied Biosystems 477A Protein Sequencer, are available commercially. Analysis of lead candidates from such binding assays using NMR spectroscopy are described in U.S. Pat. No. 5,877,030, the contents of which are incorporated herein by reference. In this way, the sequence or composition of the compounds which bind to the column can be deduced. This method allows one to determine the preferred binding partners of the ligand binding site.

Thus as stated above, a second criteria which putative MPL receptor antagonists must meet is the ability to compete with native thrombopoietin for binding to MPL receptor. A second useful screen in the identification of MPL antagonists is the ability of the library member to bind to MPL receptor in the presence of thrombopoietin and its ability, at a reasonable physiological concentration, to preclude thrombopoietin binding to MPL receptor.

Binding partner screens can then be followed by screens for biological antagonist activity. An MPL antagonist can be defined as a compound which, while capable of binding MPL receptor, does not stimulate megakaryocyte development, differentiation or proliferation. One way of testing putatively useful agents is to perform in vitro assays in which platelets or platelet precursors (e.g., megakaryocytes, or megakaryocyte precursors) are exposed to a compound after which their morphology (for example using an appropriate cell staining technique such as Wright's stain), number (for example using a Coulter counter) and/or colony forming ability are tested. Stimulation and inhibition of megakaryocyte development, differentiation or proliferation involves the use of vitro clonogenic assays. Such assays can be performed using either cell lines known to express a functional MPL receptor, several of which have been established in the prior art and examples of which include the Ba/F3 and UT-7/GM cell line, or primary hemopoietic tissue, such as bone marrow. The number and quality of megakaryocyte colonies can be determined as a function of the presence and absence of the library member. Preferably, the assays are carried out by culturing the cells in a semi-solid culture in an amount of thrombopoietin sufficient to stimulate maximal megakaryocyte colony growth from the cell population. The library member is then titrated into the cultures in order to determine the amount necessary to reduce megakaryocyte colony formation. In this manner, in addition to the amount of antagonist necessary to inhibit megakaryocyte growth altogether, one can also determine that amount which inhibits the growth by a particular percentage. For example, if it desirable to reduce megakaryocyte growth and proliferation by 50% in order to achieve a reduction in platelet count in vivo, then the assay can be used to determine that amount of antagonist necessary to inhibit megakaryocyte colony growth by 50%. An important benefit of a clonogenic assay, such as that described herein, is the ability to analyze the effect of the library member on a wide variety of hemopoietic cell types. Since it is possible, with a correct cocktail of growth factors, to stimulate the growth of a variety of hemopoietic lineages in culture, the effect of the library member on each lineage can be studied. Thus, library members can be further screened for their selective action on the megakaryoctye lineage. Clonogenic assays such as those described herein are routinely employed by artisans of ordinary skill. Each of the afore-mentioned in vitro screening assays is amenable to high-throughput screening.

Another way of measuring the biological antagonist activity of the synthetic compound is to perform in vivo assays in which animals, preferably mice, are injected, for example intravenously, with the compound and then analyzed for megakaryocyte growth and proliferation or platelet production. Hemopoietic populations, such as bone marrow and spleen, can be harvested from treated animals and plated into in vitro semi-solid clonogenic cultures in order to determine the effect of the library member on megakaryocytes. Preferably the number and quality of megakaryocyte colonies derived from test animals should be compared to that of animals injected with control carrier (i.e., saline). Alternatively, animals can be assayed directly for platelet counts. This can be done in a number of ways including by bleeding the animals (usually from the tail or retro-orbital vein) and counting the number of platelets either manually using a hemocytometer or through the use of an automated cell counter, such as a Coulter counter. Adverse side effects can also be tested in animals injected with putative antagonists in this manner. One possible adverse side effect may be an inability to clot due to a severe reduction in platelets. To assess clotting function, standard bleeding assays can be employed which measure the time required for bleeding from a experimentally induced wound to clot and thus stop. Platelet count and bleeding assays are routinely performed in human subjects as a measure of platelet count and platelet activity. Human subjects with a platelet count of more than $100 \times 10^3$ platelets per $\mu l$ of blood are generally asymptomatic and their bleeding times are within the normal range. Bleeding times of less than 10 minutes are considered normal. When platelet count falls below $100 \times 10^3$ platelets per $\mu l$, the bleeding time is extended and appears to be linearly related to the platelet count. Human subjects with a platelet count of less than $50 \times 10^3$ platelets per $\mu l$ experience easy bruising, while those with a platelet count of less than $25 \times 10^3$ platelets per $\mu l$ are prone to spontaneous internal bleeding. Platelet count and bleeding assays are routinely practiced by those of ordinary skill in the art and are taught in *Harrison's Principles of Internal Medicine*, Isselbacher, McGraw Hill, New York (1994).

Other agents which are preferred are those which bind to thrombopoietin in such a manner as to preclude or significantly interfere with its binding to MPL receptor. As stated earlier, these agents may be those which bind to a site on thrombopoietin which is involved in binding to the MPL receptor. Alternatively, they may be bind another region of thrombopoietin and in doing so cause a conformational change in the three dimensional structure of thrombopoietin which abrogates or at a minimum reduces its affinity for MPL receptor. Methods for generating ligand antagonists, particularly thrombopoietin antagonists are described in U.S. Pat. No. 5,506,107. Methods for generating antibodies to thrombopoietin are disclosed in U.S. Pat. No. 5,830,647, which also discloses the nucleic acid and amino acid sequence of thrombopoietin. The antibodies so generated were screened for agonist activity, however, it is possible to use the same approach in order to identify antagonists.

Subjects can also be administered agents which mimic the extracellular domain of MPL. The MPL receptor has been cloned and sequenced and the extracellular domain has been identified. Thus it is well within the scope of the ordinary artisan to prepare agents comprising the extracellular domain of MPL receptor and perhaps more preferably, agents which comprise the thrombopoietin binding domain of MPL receptor. MPL receptor sequence has been disclosed in PCT Patent Application WO 92/07074. Fusion proteins incorporating the extracellular domain of MPL receptor are also useful agents, particularly those which serve to stabilize, limit clearance of and thereby extend the in vivo half-life of the MPL receptor extracellular domain. Administration of the extracellular domain in vivo or a fusion thereof would function to saturate unbound thrombopoietin in the serum, thereby reducing the amount of thrombopoietin available to bind to megakaryoctye or platelet presented MPL receptor.

Screening assays for compounds which bind to thrombopoietin and thereby interfere with the binding of thrombopoietin to MPL receptor can be performed using techniques similar to those described above. The binding assays provided are modified by using a thrombopoietin molecule as the binding partner rather than a MPL receptor as is described in the afore-mentioned assays. Screening assays that are particularly useful include (1) those which determine the capacity of compounds to bind to thrombopoietin or an MPL receptor binding fragment of thrombopoietin, (2) those which determine the ability of compounds to interfere with binding of thrombopoietin to MPL receptor, and (3) those which assay the biological effect of the compound on (a) development, differentiation and proliferation of megakaryocytes (b) viability of platelets and (c) viability and development of other hemopoietic and non-hemopoietic cell types. All these screening assays have been described with relation to MPL receptor antagonists. One of ordinary skill in the art would know how to manipulate such assays for the purpose of measuring thrombopoietin antagonists.

Physical methods also exist for reducing platelet count. These methods include platelet-pheresis which is the centrifugal separation of platelets from other blood cellular components. Platelet-pheresis provides the benefit of effecting platelet reduction in a short period of time. This may be desirable for a subject unexpectedly scheduled for an elective surgery. Other physical methods for reducing platelet count involve the use of adsorption of platelets onto solid state matrices coated with binding partners specific for platelets. As an example, platelets may be removed from blood using positive selection affinity filtration. Such an approach may involve applying peripheral blood to a column containing a solid matrix to which is coupled a growth factor such as thrombopoietin. Another example of affinity chromatography may involve elution of blood over an affinity matrix, having as the solid state Sephadex G-10, coated with fibrinogen, fibronectin, or preferably, an Arg-Gly-Asp tripeptide, all of which are known to bind platelets. This latter approach has been reported by Besselink et al. for binding of human platelets. (J. Biomater. Sci. Polym. Ed. 1995 7:55 1562) Other binding partners for platelets which could be used in an adsorption technique to separate platelets from blood are glycoprotein IIb/IIIa antagonists such as Ro-43-8857 and L-700,462 reported by Cook et al. (Thromb. Haemost. 1993 70:838–47) Yet another form of affinity separation useful in the removal of platelets from blood is immune affinity which uses a solid matrix coupled to an antibody specific for platelets and/or megakaryocytes such as an anti-glycoprotein IIb/IIIa receptor, or a fragment thereof.

Thus, in this aspect of the invention, a subject's blood is removed, depleted of platelets, and then returned until overall platelet count is below normal.

The invention further embraces pharmaceutical preparations of agents which reduce platelet count. In particular, pharmaceutical preparations are provided which comprise agents which bind to MPL receptor, either extracellularly or intracellularly, agents which interfere with signal transduction from the MPL receptor, agents which bind to thrombopoietin, agents which bind to an intracellular tyrosine kinase that modulates signal transduction from an MPL receptor, and agents which inhibit the binding of a thrombopoietin molecule to an MPL receptor. An agent such as those described above are present in the pharmaceutical preparation in an amount effective to reduce platelet count in a subject. Depending on subject to be treated and the severity of the disorder to be treated, the agent may be provided in an amount to reduce platelet count by any amount and more preferably by at least 5%, at least 10%, at least 20%, at least 30%, at least 40%, at least 50%, at least 60%, at least 70%, at least 80%, at least 90% or at least 95%. In addition, the pharmaceutical preparation will also contain a pharmaceutically acceptable carrier.

The invention provides pharmaceutical preparations of the agents of the invention. These pharmaceutical preparations comprise the agent of the invention and also a pharmaceutically acceptable carrier. The pharmaceutical preparations may be administered in effective amounts. The effective amount will depend upon the mode of administration, the particular condition being treated and the desired outcome. It will also depend upon, as discussed above, the stage of the condition, the age and physical condition of the subject, the nature of concurrent therapy, if any, and like factors well known to the medical practitioner. For prophylactic applications, it is that amount sufficient to delay the onset of, inhibit the progression of, or halt altogether the particular condition being treated, thereby producing patient benefit. For therapeutic applications, it is that amount sufficient to achieve a medically desirable result, thereby producing patient benefit. In some instances, patient benefit may be measured by a reduction in morbidity and/or mortality. In some cases this is a decrease in cell maturation and/or proliferation. In the case of megakaryocytes, the medically desirable result may be to inhibit thrombosis via blocking of megakaryoctye maturation, endoreduplication and/or proliferation. In other cases, it is an increase in platelet consumption, elimination or death. Ultimately, the amount which is administered is one effective for reducing platelet count to low normal and more preferably below normal levels in a subject, without a significant level of adverse side effects.

Generally, doses of active compounds of the present invention would be from about 0.01 mg/kg per day to 1000 mg/kg per day. It is expected that daily doses ranging from 1–500 mg/kg, and preferably doses ranging from 1–100 mg/kg, and even more preferably doses ranging from 0.001–50 mg/kg, and most preferably doses ranging from 0.001–10 mg/kg will be suitable. A variety of administration routes are available. The methods of the invention, generally speaking, may be practiced using any mode of administration that is medically acceptable, meaning any enteral or parenteral mode that produces effective levels of the active compounds without causing clinically unacceptable adverse effects. Such modes of administration include oral, rectal, topical, nasal, intrapulmonary, intracavitary, transdermal, interdermal, transmucosal, subcutaneous, intravenous, intraarterial, intramuscular, or local routes. The term "parenteral" includes subcutaneous, intravenous, intramuscular, or infusion. Injectable routes such as intravenous or intramuscular routes are not particularly suitable for long-term therapy and prophylaxis. They could, however, be preferred in emergency situations. Oral administration will be preferred for prophylactic or therapeutic treatment because of the convenience to the patient as well as the dosing schedule.

When peptides are used therapeutically, in certain embodiments a desirable route of administration is by pulmonary aerosol. Techniques for preparing aerosol delivery systems containing peptides are well known to those of skill in the art. Generally, such systems should utilize components which will not significantly impair the biological properties of the peptides, for example the paratope binding capacity of antibodies (see, for example, Sciarra and Cutie, "Aerosols," in *Remington's Pharmaceutical Sciences*, 18th edition, 1990, pp 1694–1712; incorporated by reference). Those of skill in the art can readily determine the various parameters and conditions for producing peptide aerosols without resort to undue experimentation.

Compositions suitable for oral administration may be presented as discrete units, in both immediate release or controlled release formulations, such as capsules, tablets, lozenges, each containing a predetermined amount of the active agent. Other compositions include suspensions in aqueous liquids or non-aqueous liquids such as a syrup, elixir or an emulsion.

Preparations for parenteral administration include sterile aqueous or non-aqueous solutions, suspensions, and emulsions as well as injectable drug delivery devices such as controlled release preparations. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

The agents that reduce platelet count may be combined, optionally, with a pharmaceutically-acceptable carrier. The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the agents of the present invention, and with each other, in a manner such that there is no interaction which would substantially impair the desired pharmaceutical efficacy.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Other delivery systems can include immediate release or controlled release formulations. Examples of controlled release formulations include time-release, delayed release or sustained release delivery systems. Such systems can reduce toxicity, increase efficacy and avoid repeated administrations of the platelet reducing agent, reducing peak-related side effects and increasing convenience to the subject and the physician. Many types of release delivery systems are available and known to those of ordinary skill in the art. They include but are not limited to polymer base systems such as poly(lactide-glycolide), copolyoxalates, polycaprolactones, lipids, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189 and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant (or device) may be particularly suitable for treatment of subjects at elevated risk of a vaso-occlusive event such as one resulting from a thrombotic event. These subjects would include subjects scheduled for elective vascular surgery. Long-term release, as used herein, means that the implant is constructed and arranged to deliver levels of the active ingredient for at least 1 week, in some instances for at least 30 days, and in others for at least 60 days. In some aspects of the invention that involve longer-term treatment and prevention, it is desirable that the sustained release device release effective amounts of agent for at least 6 months, 1 year, 2 years or in some cases, 5 years or more. Long-term sustained release implants are well-known to those of ordinary skill in the art and include some of the release systems described above.

Regardless of the particular agent used in the methods of the invention, administration via a sustained release device is preferable in some instances because it reduces the peak levels of agent which are often observed with single bolus administrations (such as non-continuous injection or oral delivery). A reduction in the peak level of agent in the subject also reduces the likelihood of side effects.

The agent of the invention should be administered for a length of time sufficient to provide either or both therapeutic and prophylactic benefit to the subject. Generally, the agent is administered for at least one day. In some instances, particularly where a subject has had a vaso-occlusive event or where the subject is at risk of such an event, the agent may be administered for the remainder of the subject's life. The rate at which the agent is administered may vary depending upon the needs of the subject and the mode of administration. For example, it may be necessary in some instances to administer higher and more frequent doses of the agent to a subject for example during or immediately following a vaso-occlusive event (such as a myocardial infarction), provided still that such doses reduce platelet count but do not significantly affect platelet function. On the other hand, it may be desirable to administer lower doses in order to maintain a desired platelet count once it is achieved. In still other embodiments, the same dose of agent may be administered throughout the treatment period which as described herein may extend throughout the lifetime of the subject. The frequency of administration may vary depending upon the characteristics of the subject. The agent may be administered daily, every 2 days, every 3 days, every 4 days, every 5 days, every week, every 10 days, every 2 weeks, every month, or more, or any time therebetween as if such time was explicitly recited herein.

In other aspects, the agents of the invention are administered with another agent, preferably an agent that would normally be indicated for the subject. In some embodiments, the agents may be administered substantially simultaneously with the other therapeutic agents. By substantially simultaneously, it is meant that a platelet reducing agent of the invention is administered to a subject close enough in time with the administration of the other therapeutic agent, whereby the two compounds may exert an additive or even synergistic effect, e.g., reducing platelet function by decreasing platelet count and inhibiting their ability to aggregate. In other embodiments, the platelet reducing agents of the invention be administered before or after the administration of the other therapeutic agent.

The agents of the invention may be administered with several categories of therapeutic agents, although preferably these agents are those which would normally be indicated for the subject. Generally, these agents are those which are useful and which are currently indicated for treating vascular disorders and vascular complications. These agents can be classified in terms of their function or in terms of the disorders for which they are indicated. Several useful categories of such agents include but are not limited to anti-inflammatory agents, anti-thrombotic agents, anti-platelet agents, fibrinolytic agents, lipid reducing agents, direct thrombin inhibitors, glycoprotein IIb/IIIa receptor inhibitors, agents that binds to cellular adhesion molecules and inhibit the ability of white blood cells to attach to such molecules, calcium channel blockers, beta-adrenergic receptor blockers, cyclooxygenase-2 inhibitors, and angiotensin system inhibitors.

One broad category agents which may be administered with the platelet reducing agents of the invention is anti-thrombotic agents. Anti-thrombotic agents are defined as agents which prevent the formation of a blood thrombus via a number of potential mechanisms and they include fibrinolytic agents, anti-coagulant agents and inhibitors of platelet function.

Fibrinolytic agents are defined as agent that lyse a thrombus (e.g., a blood clot), usually through the dissolution of fibrin by enzymatic action. Examples of thrombolytic agents include but are not limited to ancrod, anistreplase, bisobrin lactate, brinolase, Hageman factor (i.e. factor XII) fragments, molsidomine, plasminogen activators such as streptokinase, tissue plasminogen activators (TPA) and urokinase, and plasmin and plasminogen. Anticoagulant agents also include inhibitors of factor Xa, factor TFPI, factor VIIa, factor IXc, factor Va, factor VIIIa as well as inhibitors of other coagulation factors.

Anti-coagulant agents are agents which inhibit the coagulation pathway by impacting negatively upon the production, deposition, cleavage and/or activation of factors essential in the formation of a blood clot. Anti-coagulant agents include but are not limited to vitamin K antagonists such as coumarin and coumarin derivatives (e.g., warfarin sodium); glycosoaminoglycans such as heparins both in unfractionated form and in low molecular weight form; ardeparin sodium, bivalirudin, bromindione, coumarin dalteparin sodium, desirudin, dicumarol, lyapolate sodium, nafamostat mesylate, phenprocoumon, sulfatide, and tinzaparin sodium.

Other "anti-coagulant" and/or "fibrinolytic" agents include Plasminogen (to plasmin via interactions of prekallikrein, kininogens, Factors XII, XIIIa, plasminogen proactivator, and tissue plasminogen activator[TPA]) Streptokinase; Urokinase: Anisoylated Plasminogen-Streptokinase Activator Complex; Pro-Urokinase; (Pro-UK); rTPA (alteplase or activase; r denotes recombinant); rPro-UK; Abbokinase; Eminase; Sreptase Anagrelide Hydrochloride; Bivalirudin; Dalteparin Sodium; Danaparoid Sodium; Dazoxiben Hydrochloride; Efegatran Sulfate; Enoxaparin Sodium; Ifetroban; Ifetroban Sodium; Tinzaparin Sodium; retaplase; Trifenagrel; Warfarin; Dextrans.

Still other anti-coagulant agents include, but are not limited to, Ancrod; Anticoagulant Citrate Dextrose Solution; Anticoagulant Citrate Phosphate Dextrose Adenine Solution; Anticoagulant Citrate Phosphate Dextrose Solution; Anticoagulant Heparin Solution; Anticoagulant Sodium Citrate Solution; Ardeparin Sodium; Bivalirudin; Bromindione; Dalteparin Sodium; Desirudin; Dicumarol; Heparin Calcium; Heparin Sodium; Lyapolate Sodium; Nafamostat Mesylate; Phenprocoumon; Tinzaparin Sodium; Warfarin Sodium.

Heparin may stabilize symptoms in evolving stroke, but anti-coagulants are useless (and possibly dangerous) in acute completed stroke, and are contraindicated in hypertensives because of the increased possibility of hemorrhage into the brain or other organs. Although the timing is controversial, anti-coagulants may be started to prevent recurrent cardiogenic emboli. Clot lysing agents, including tissue plasminogen activator and streptokinase, are being evaluated for the very early treatment of acute stroke. Nimodipine has recently been shown to improve survival and clinical outcome after ischemic stroke.

Inhibitors of platelet function are agents that impair the ability of mature platelets to perform their normal physiological roles (i.e., their normal function). Platelets are normally involved in a number of physiological processes such as adhesion, for example, to cellular and non-cellular entities, aggregation, for example, for the purpose of forming a blood clot, and release of factors such as growth factors (e.g., platelet-derived growth factor (PDGF)) and platelet granular components. One subcategory of platelet function inhibitors are inhibitors of platelet aggregation which are compounds which reduce or halt the ability of platelets to associate physically with themselves or with other cellular and non-cellular components, thereby precluding the ability of a platelet to form a thrombus.

Examples of useful inhibitors of platelet function include but are not limited to acadesine, anagrelide (if given at doses exceeding 10 mg/day), anipamil, argatroban, aspirin, clopidogrel, cyclooxygenase inhibitors such as nonsteroidal anti-inflammatory drugs and the synthetic compound FR-122047, danaparoid sodium, dazoxiben hydrochloride, diadenosine 5',5'''-P1,P4-tetraphosphate (Ap4A) analogs, difibrotide, dilazep dihydrochloride, 1,2- and 1,3-glyceryl dinitrate, dipyridamole, dopamine and 3-methoxytyramine, efegatran sulfate, enoxaparin sodium, glucagon, glycoprotein IIb/IIIa antagonists such as Ro-43-8857 and L-700,462, ifetroban, ifetroban sodium, iloprost, isocarbacyclin methyl ester, isosorbide-5-mononitrate, itazigrel, ketanserin and BM-13.177, lamifiban, lifarizine, molsidomine, nifedipine, oxagrelate, PGE, platelet activating factor antagonists such as lexipafant, prostacyclin ($PGI_2$), pyrazines, pyridinol carbamate, ReoPro (i.e., abciximab), sulfinpyrazone, synthetic compounds BN-50727, BN-52021, CV-4151, E-5510, FK-409, GU-7, KB-2796, KBT-3022, KC-404, KF-4939, OP-41483, TRK-100, TA-3090, TFC-612 and ZK-36374, 2,4,5,7-tetrathiaoctane, 2,4,5,7-tetrathiaoctane 2,2-dioxide, 2,4,5-trithiahexane, theophyllin pentoxifyllin, thromboxane and thromboxane synthetase inhibitors such as picotamide and sulotroban, ticlopidine, tirofiban, trapidil and ticlopidine, trifenagrel, trilinolein, 3-substituted 5,6-bis(4-methoxyphenyl)-1,2,4-triazines, and antibodies to glycoprotein IIb/IIIa as well as those disclosed in U.S. Pat. No. 5,440,020, and anti-serotonin drugs, Clopridogrel; Sulfinpyrazone; Aspirin; Dipyridamole; Clofibrate; Pyridinol Carbamate; PGE; Glucagon; Antiserotonin drugs; Caffeine; Theophyllin Pentoxifyllin; Ticlopidine.

"Anti-inflammatory" agents include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac;

Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium. One preferred antiinflammatory agent is aspirin.

"Lipid reducing" agents include gemfibrozil, cholystyramine, colestipol, nicotinic acid, probucol lovastatin, fluvastatin, simvastatin, atorvastatin, pravastatin, cirivastatin.

"Direct thrombin inhibitors" include hirudin, hirugen, hirulog, agatroban, PPACK, thrombin aptamers. "Glycoprotein IIb/IIIa receptor inhibitors" are both antibodies and non-antibodies, and include but are not limited to ReoPro (abcixamab), lamifiban, tirofiban.

"Calcium channel blockers" are a chemically diverse class of compounds having important therapeutic value in the control of a variety of diseases including several cardiovascular disorders, such as hypertension, angina, and cardiac arrhythmias (Fleckenstein, *Cir. Res.* v. 52, (suppl. 1), p.13–16 (1983); Fleckenstein, *Experimental Facts and Therapeutic Prospects*, John Wiley, New York (1983); McCall, D., *Curr Pract Cardiol*, v. 10, p. 1–11 (1985)). Calcium channel blockers are a heterogeneous group of drugs that prevent or slow the entry of calcium into cells by regulating cellular calcium channels. (Remington, *The Science and Practice of Pharmacy*, Nineteenth Edition, Mack Publishing Company, Eaton, PA, p.963 (1995)). Most of the currently available calcium channel blockers, and useful according to the present invention, belong to one of three major chemical groups of drugs, the dihydropyridines, such as nifedipine, the phenyl alkyl amines, such as verapamil, and the benzothiazepines, such as diltiazem. Other calcium channel blockers useful according to the invention, include, but are not limited to, amrinone, amlodipine, bencyclane, felodipine, fendiline, flunarizine, isradipine, nicardipine, nimodipine, perhexilene, gallopamil, tiapamil and tiapamil analogues (such as 1993RO-11-2933), phenytoin, barbiturates, and the peptides dynorphin, omega-conotoxin, and omega-agatoxin, and the like and/or pharmaceutically acceptable salts thereof. "Beta-adrenergic receptor blocking agents" are a class of drugs that antagonize the cardiovascular effects of catecholamines in angina pectoris, hypertension, and cardiac arrhythmias. Beta-adrenergic receptor blockers include, but are not limited to, atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitrilHCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl2-thienyl)thiazol,7-(2-hydroxy-3-t-butylaminpropoxy) phthalide. The above-identified compounds can be used as isomeric mixtures, or in their respective levorotating or dextrorotating form.

Cyclooxygenase-2 (COX-2) is a recently identified form of a cyclooxygenase. "Cyclooxygenase-" is an enzyme complex present in most tissues that produces various prostaglandins and thromboxanes from arachidonic acid. Non-steroidal, anti-inflammatory drugs exert most of their anti-inflammatory, analgesic and antipyretic activity and inhibit hormone-induced uterine contractions and certain types of cancer growth through inhibition of the cyclooxygenase (also known as prostaglandin G/H synthase and/or prostaglandinendoperoxide synthase). Initially, only one form of cyclooxygenase was known, the "constitutive enzyme" or cyclooxygenase-1 (COX-1). It and was originally identified in bovine seminal vesicles.

Cyclooxygenase-2 (COX-2) has been cloned, sequenced and characterized initially from chicken, murine and human sources (See, e.g., U.S. Pat. No. 5,543,297, issued Aug. 6, 1996 to Cromlish, et al., and assigned to Merck Frosst Canada, Inc., Kirkland, Calif., entitled: "Human cyclooxygenase-2 cDNA and assays for evaluating cyclooxygenase-2 activity"). This enzyme is distinct from the COX-1. COX-2 is rapidly and readily inducible by a number of agents including mitogens, endotoxin, hormones, cytokines and growth factors. As prostaglandins have both physiological and pathological roles, the constitutive enzyme, COX-1, is responsible, in large part, for endogenous basal release of prostaglandins and hence is important in their physiological functions such as the maintenance of gastrointestinal integrity and renal blood flow. By contrast, it is believed that the inducible form, COX-2, is mainly responsible for the pathological effects of prostaglandins where rapid induction of the enzyme would occur in response to such agents as inflammatory agents, hormones, growth factors, and cytokines. Therefore, it is believed that a selective inhibitor of COX-2 has similar anti-inflammatory, antipyretic and analgesic properties to a conventional non-steroidal anti-inflammatory drug, and in addition inhibits hormone-induced uterine contractions and also has potential anti-cancer effects, but with reduced side effects. In particular, such COX-2 inhibitors are believed to have a reduced potential for gastrointestinal toxicity, a reduced potential for renal side effects, a reduced effect on bleeding times and possibly a decreased potential to induce asthma attacks in aspirin-sensitive asthmatic subjects, and are therefore useful according to the present invention.

A number of selective "COX-2 inhibitors" are known in the art. These include, but are not limited to, COX-2 inhibitors described in U.S. Pat. No. 5,474,995 "Phenyl heterocycles as cox-2 inhibitors"; U.S. Pat. No. 5,521,213 "Diaryl bicyclic heterocycles as inhibitors of cyclooxygenase-2"; U.S. Pat. No. 5,536,752 "Phenyl heterocycles as COX-2 inhibitors"; U.S. Pat. No. 5,550,142 "Phenyl heterocycles as COX-2 inhibitors"; U.S. Pat. No. 5,552,422 "Aryl substituted 5,5 fused aromatic nitrogen compounds as anti-inflammatory agents"; U.S. Pat. No. 5,604,253 "N-benzylindol-3-yl propanoic acid derivatives as cyclooxygenase inhibitors"; U.S. Pat. No. 5,604,260 "5-methanesulfonamido-1-indanones as an inhibitor of cyclooxygenase-2"; U.S. Pat. No. 5,639,780 N-benzyl indol-3-yl butanoic acid derivatives as cyclooxygenase inhibitors"; U.S. Pat. No. 5,677,318 Diphenyl-1,2-3-thiadiazoles as anti-inflammatory agents"; U.S. Pat. No. 5,691,374 "Diaryl-5-oxygenated-2-(5H) -furanones as COX-2 inhibitors"; U.S. Pat. No. 5,698,584 "3,4-diaryl-2-hydroxy-2,5-dihydrofurans as prodrugs to COX-2 inhibitors"; U.S. Pat. No. 5,710,140 "Phenyl heterocycles as COX-2 inhibitors"; U.S. Pat. No. 5,733,909 "Diphenyl stilbenes as prodrugs to COX-2 inhibitors"; U.S. Pat. No. 5,789,413 "Alkylated styrenes as prodrugs to COX-2 inhibitors"; U.S. Pat. No. 5,817,700 "Bisaryl cyclobutenes derivatives as cyclooxygenase inhibitors"; U.S. Pat. No. 5,849,943 "Stilbene derivatives useful as cyclooxygenase-2 inhibitors"; U.S. Pat. No. 5,861,419 "Substituted pyridines as selective cyclooxygenase-2 inhibitors"; U.S. Pat. No. 5,922,742 "Pyridinyl-2-cyclopenten-1-ones as selective cyclooxygenase-2 inhibitors"; U.S. Pat. No. 5,925,631 "Alkylated styrenes as prodrugs to COX-2 inhibitors"; all of which are commonly assigned to Merck Frosst Canada, Inc. (Kirkland, Calif.). Additional COX-2 inhibitors are also described in U.S. Pat. No. 5,643,933, assigned to G. D. Searle & Co. (Skokie, Ill.), entitled: "Substituted sulfonylphenylheterocycles as cyclooxygenase-2 and 5-lipoxygenase inhibitors."

A number of the above-identified COX-2 inhibitors are prodrugs of selective COX-2 inhibitors, and exert their action by conversion in vivo to the active and selective COX-2 inhibitors. The active and selective COX-2 inhibitors formed from the above-identified COX-2 inhibitor prodrugs are described in detail in WO 95/00501, published Jan. 5, 1995, WO 95/18799, published Jul. 13, 1995 and U.S. Pat. No. 5,474,995, issued Dec. 12, 1995. Given the teachings of U.S. Pat. No. 5,543,297, entitled: "Human cyclooxygenase-2 cDNA and assays for evaluating cyclooxygenase-2 activity," a person of ordinary skill in the art would be able to determine whether an agent is a selective COX-2 inhibitor or a precursor of a COX-2 inhibitor, and therefore part of the present invention.

An "angiotensin system inhibitor" is an agent that interferes with the function, synthesis or catabolism of angiotensin II. These agents include, but are not limited to, angiotensin-converting enzyme (ACE) inhibitors, angiotensin II antagonists, angiotensin II receptor antagonists, agents that activate the catabolism of angiotensin II, and agents that prevent the synthesis of angiotensin I from which angiotensin II is ultimately derived. The renin-angiotensin system is involved in the regulation of hemodynamics and water and electrolyte balance. Factors that lower blood volume, renal perfusion pressure, or the concentration of $Na^+$ in plasma tend to activate the system, while factors that increase these parameters tend to suppress its function.

Angiotensin I and angiotensin II are synthesized by the enzymatic renin-angiotensin pathway. The synthetic process is initiated when the enzyme renin acts on angiotensinogen, a pseudoglobulin in blood plasma, to produce the decapeptide angiotensin I. Angiotensin I is converted by angiotensin converting enzyme (ACE) to angiotensin II (angiotensin-[1-8] octapeptide). The latter is an active pressor substance which has been implicated as a causative agent in several forms of hypertension in various mammalian species, e.g., humans.

Angiotensin (renin-angiotensin) system inhibitors are compounds that act to interfere with the production of angiotensin II from angiotensinogen or angiotensin I or interfere with the activity of angiotensin II. Such inhibitors are well known to those of ordinary skill in the art and include compounds that act to inhibit the enzymes involved in the ultimate production of angiotensin II, including renin and ACE. They also include compounds that interfere with the activity of angiotensin II, once produced. Examples of classes of such compounds include antibodies (e.g., to renin), amino acids and analogs thereof (including those conjugated to larger molecules), peptides (including peptide analogs of angiotensin and angiotensin I), pro-renin related analogs, etc. Among the most potent and useful renin-angiotensin system inhibitors are renin inhibitors, ACE inhibitors, and angiotensin II antagonists. In a preferred embodiment of the invention, the renin-angiotensin system inhibitors are renin inhibitors, ACE inhibitors, and angiotensin II antagonists.

"Angiotensin II antagonists" are compounds which interfere with the activity of angiotensin II by binding to angiotensin II receptors and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid; stability can be enhanced by other replacements that slow degeneration in vivo. Examples of angiotensin II antagonists include: peptidic compounds (e.g., saralasin, [(San$^1$)(Val$^5$)(Ala$^8$)] angiotensin -(1-8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., *J Pharmacol Exp. Ther.* 247(1), 1–7 (1988)); 4,5,6,7-tetrahydro-1H-imidazo [4,5-c] pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(-1-naphthyl)-L-alanyl-(4, thiazolyl)-L-alanyl (35, 45)-4-amino-3-hydroxy-5-cyclo-hexapentanoyl-N-hexylamide, Sankyo Company, Ltd., Tokyo, Japan); SKF108566 (E-alpha-2-[2-butyl-1-(carboxy phenyl) methyl] 1H-imidazole-5-yl[methylane]-2-thiophenepropanoic acid, Smith Kline Beecham Pharmaceuticals, PA); Losartan (DUP753/MK954, DuPont Merck Pharmaceutical Company); Remikirin (RO42-5892, F. Hoffman LaRoche AG); $A_2$ agonists (Marion Merrill Dow) and certain non-peptide heterocycles (G.D.Searle and Company).

"Angiotensin converting enzyme (ACE), is an enzyme which catalyzes the conversion of angiotensin I to angiotensin II. ACE inhibitors include amino acids and derivatives thereof, peptides, including di- and tri- peptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

"Renin inhibitors" are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di- and tri- peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075,451); fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437).

Agents that bind to cellular adhesion molecules and inhibit the ability of white blood cells to attach to such molecules include polypeptide agents. Such polypeptides include polyclonal and monoclonal antibodies, prepared according to conventional methodology. Such antibodies already are known in the art and include anti-ICAM 1 antibodies as well as other such antibodies (see earlier discussion on antibodies).

Other than aspirin, ticlopidine is another antiplatelet agent that has been shown to be beneficial for stroke treatment. Endarterectomy may be indicated in patients with 70 to 99 percent narrowing of a symptomatic internal carotid artery. However, most authorities agree that carotid endarterectomy is not indicated in patients with TIAs that are referable to the basilar-vertebral system, in patients with significant deficits from prior strokes, or in patients in whom a stroke is evolving.

HMG-CoA (3-hydroxy-3-methylglutaryl-coenzyme A) reductase is the microsomal enzyme that catalyzes the rate limiting reaction in cholesterol biosynthesis (HMG-CoA6Mevalonate). An HMG-CoA reductase inhibitor inhibits HMG-CoA reductase, and as a result inhibits the synthesis of cholesterol. A number of HMG-CoA reductase inhibitors has been used to treat individuals with hypercholesterolemia. More recently, HMG-CoA reductase inhibitors have been shown to be beneficial in the treatment of stroke (Endres M, et al., *Proc Natl Acad Sci U.S.A*, 1998, 95:8880–5).

HMG-CoA reductase inhibitors useful for co-administration with the agents of the invention include, but are not limited to, simvastatin (U.S. Pat. No. 4,444,784), lovastatin (U.S. Pat. No. 4,231,938), pravastatin sodium (U.S. Pat. No. 4,346,227), fluvastatin (U.S. Pat. No. 4,739,073), atorvastatin (U.S. Pat. No. 5,273,995), cerivastatin, and numerous others described in U.S. Pat. No. 5,622,985, U.S. Pat. No. 5,135,935, U.S. Pat. No. 5,356,896, U.S. Pat. No. 4,920,109, U.S. Pat. No. 5,286,895, U.S. Pat. No. 5,262,435, U.S. Pat. No. 5,260,332, U.S. Pat. No. 5,317,031, U.S. Pat. No. 5,283,256, U.S. Pat. No. 5,256,689, U.S. Pat. No. 5,182,298, U.S. Pat. No. 5,369,125, U.S. Pat. No. 5,302,604, U.S. Pat. No. 5,166,171, U.S. Pat. No. 5,202,327, U.S. Pat. No. 5,276,021, U.S. Pat. No. 5,196,440, U.S. Pat. No. 5,091,386, U.S. Pat. No. 5,091,378, U.S. Pat. No. 4,904,646, U.S. Pat. No. 5,385,932, U.S. Pat. No. 5,250,435, U.S. Pat. No. 5,132,312, U.S. Pat. No. 5,130,306, U.S. Pat. No. 5,116,870, U.S. Pat. No. 5,112,857, U.S. Pat. No. 5,102,911, U.S. Pat. No. 5,098,931, U.S. Pat. No. 5,081,136, U.S. Pat. No. 5,025,000, U.S. Pat. No. 5,021,453, U.S. Pat. No. 5,017,716, U.S. Pat. No. 5,001,144, U.S. Pat. No. 5,001,128, U.S. Pat. No. 4,997,837, U.S. Pat. No. 4,996,234, U.S. Pat. No. 4,994,494, U.S. Pat. No. 4,992,429, U.S. Pat. No. 4,970,231, U.S. Pat. No. 4,968,693, U.S. Pat. No. 4,963,538, U.S. Pat. No. 4,957,940, U.S. Pat. No. 4,950,675, U.S. Pat. No. 4,946,864, U.S. Pat. No. 4,946,860, U.S. Pat. No. 4,940,800, U.S. Pat. No. 4,940,727, U.S. Pat. No. 4,939,143, U.S. Pat. No. 4,929,620, U.S. Pat. No. 4,923,861, U.S. Pat. No. 4,906,657, U.S. Pat. No. 4,906,624 and U.S. Pat. No. 4,897,402, the disclosures of which patents are incorporated herein by reference.

Nitric oxide (NO) has been recognized as a messenger molecule with many physiologic roles, in the cardiovascular, neurologic and immune systems (Griffith, TM et al., *J Am Coll Cardiol*, 1988, 12:797–806). It mediates blood vessel relaxation, neurotransmission and pathogen suppression. NO is produced from the guanidino nitrogen of L-arginine by NO Synthase (Moncada, S and Higgs, E A, *Eur J Clin Invest*, 1991, 21:361–374). Agents that upregulate endothelial cell Nitric Oxide Synthase include, but are not limited to, L-arginine, rho GTPase function inhibitors (see International Application WO 99/47153, the disclosure of which is incorporated herein by reference), and agents that disrupt actin cytoskeletal organization (see International Application WO 00/03746, the disclosure of which is incorporated herein by reference).

"Co-administering," as used herein, refers to administering simultaneously two or more compounds of the invention (e.g., anagrelide, and an agent known to be beneficial in the treatment of, for example, a cardiovascular condition e.g., an anti-coagulant-), as an admixture in a single composition, or sequentially, close enough in time so that the compounds may exert an additive or even synergistic effect, i.e., on reducing cardiomyocyte cell-death in a cardiovascular condition.

It should be understood that the preceding is merely a detailed description of certain preferred embodiments. It therefore should be apparent to those of ordinary skill in the art that various modifications and equivalents can be made without departing from the spirit and scope of the invention. It is intended that the invention encompass all such modifications within the scope of the appended claims.

All references, patents and patent applications and publications that are cited or referred to in this application are incorporated in their entirety herein by reference.

I claim:

1. A method for treating a subject to inhibit a vase-occlusive event comprising administering to the subject an MPL pathway inhibitory agent in an amount effective to reduce platelet count in the subject to a low normal level.

2. The method of claim 1, wherein the vaso-occlusive event is an occlusion of a stent or an occlusion of a blood vessel.

3. The method of claim 1, wherein the vaso-occlusive event is intimal hyperplasia.

4. The method of claim 1, wherein the vaso-occlusive event is a thrombotic event.

5. The method of claim 1, wherein the subject does not have a hematological proliferative disorder.

6. The method of claim 1, wherein the subject is apparently healthy.

7. The method of claim 1, wherein the subject exhibits symptoms of a vaso-occlusive event.

8. The method of claim 1, wherein the subject has a normal platelet count.

9. The method of claim 1, wherein the subject has an abnormally elevated risk of a thrombotic event.

10. The method of claim 1, wherein the subject has vascular disease.

11. The method of claim 1, wherein the subject has had a primary vaso-occlusive event.

12. The method of claim 1, wherein the subject has a condition selected from the group consisting of hypercholesterolemia, hypertension and atherosclerosis.

13. The method of claim 1, wherein the subject will undergo an elective surgical procedure.

14. The method of claim 1, wherein platelet count is reduced by at least 20%.

15. The method of claim 1, wherein platelet count is reduced to below $250 \times 10^3$ platelets per $\mu l$.

16. The method of claim 1, wherein the MPL inhibitory agent is administered with an agent for treating vascular disorder or vascular complication.

17. The method of claim 1, wherein the MPL inhibitory agent binds to an MPL receptor.

18. The method of claim 1, wherein the MPL inhibitory agent binds to a thrombopoietin molecule.

19. The method of claim 1, wherein the platelet count is reduced to below normal levels.

20. The method of claim 4, wherein the thrombotic event is a thromboembolic event.

21. The method of claim 4, wherein the thrombotic event is a primary thrombotic event.

22. The method of claim 4, wherein the thrombotic event is a secondary thrombotic event.

23. The method of claim 4, wherein the thrombotic event is selected from the group consisting of arterial thrombosis, coronary thrombosis, venous thrombosis, microvascular thrombosis, stent thrombosis, graft thrombosis and heart valve thrombosis.

24. The method of claim 4, wherein the vaso-occlusive event is selected from the group consisting of myocardial infarction, stroke, transient ischemio attack and coronary stenosis.

25. The method of claim 1, wherein the subject is a human.

26. The method of claim 10, wherein tho vascular disease is selected from the group consisting of arteriosclerosis, cardiovascular disease, cerebrovascular disease, renovascular disease, mesenteric vascular disease, pulmonary vascular disease, ocular vascular disease and peripheral vascular disease.

27. The method of claim 1, wherein the subject has undergone a surgical procedure.

28. The method of claim 13, wherein the surgical procedure is selected from the group consisting of coronary angiography, coronary stent placement, coronary by-pass surgery, carotid artery procedure, peripheral stent placement, vascular grafting, thrombectomy, peripheral vascular surgery, vascular surgery, organ transplant, artificial heart transplant, vascular angioplasty, vascular laser therapy, vascular replacement and vascular stenting.

29. The method of claim 28, wherein the surgical procedure is selected from the group consisting of coronary angiography, coronary stent placement, coronary by-pass surgery, carotid artery procedure, peripheral stent placement, vascular grafting, thrombectomy, peripheral vascular surgery, vascular surgery, organ transplant, artificial heart transplant, vascular angloplasty, vascular laser therapy, vascular replacement and vascular stenting.

30. The method of claim 1, wherein the effective amount is in the rage of 0.001 mg/kg/day to 30 mg/kg/day.

31. The method of claim 1, wherein platelet count is reduced by at least 50%.

32. The method of claim 1, wherein platelet count is reduced to below $200 \times 10^3$ platelets per $\mu l$.

33. The method of claim 1, wherein platelet count is reduced to below $150 \times 10^3$ platelets per $\mu l$.

34. The method of claim 1, wherein platelet count is reduced to below $100 \times 10^3$ platelets per $\mu l$.

35. The method of claim 1, wherein platelet count is reduced by at least 10% and to below $200 \times 10^3$ platelets per $\mu l$.

36. The method of claim 16, wherein the agent for treating vascular disorder or vascular complication is an anti-thrombotic agent.

37. The method of claim 36, wherein the anti-thrombotic agent is selected from the group consisting of anti-coagulant agents, fibrinolytic agents and inhibitors of platelet function.

38. The method of claim 37, wherein the inhibitors of platelet function are selected from the group consisting of aspirin, abciximab, clopidogrel and dipyridamole.

39. The method of claim 37, wherein the anti-coagulant agents are selected from the group consisting of glycosoaminoglycans and vitamin K antagonists.

40. The method of claim 37, wherein the fibrinolytic agents are selected from the group consisting of plasminogen activators, plasmin and plasminogen.

41. The method of claim 40, wherein the plasminogen activators are selected from the group consisting of tissue plasminogen activator (TPA), streptokinase and urokinase.

42. The method of claim 13, wherein the MPL inhibitory agent is administered prior to the elective surgery.

43. The method of claim 1, wherein the MPL inhibitory agent is administered by a parenteral route.

44. The method of claim 1, wherein the MPL inhibitory agent is administered by an enteral route.

45. The method of claim 1, wherein the MPL inhibitory agent is administered in a sustained release device.

46. The method of claim 11, wherein the MPL inhibitory agent is administered following the primary vaso-occlusive event.

47. The method of claim 16, wherein the agent for treating vascular disorder or vascular complication is selected from the group consisting of anti-inflammatory agents, anti-thrombotic agents, anti-platelet agents, fibrinolytic agents, lipid reducing agents, direct thrombin inhibitors, glycoprotein IIb/IIIa receptor inhibitors, agents that binds to cellular adhesion molecules and inhibit the ability of white blood cells to attach to such molecules, calcium channel blockers, beta-adrenergic receptor blockers, cyclooxygenase-2 inhibitors, and angiotensin system inhibitors.

* * * * *

UNITED STATES PATENT AND TRADEMARK OFFICE
CERTIFICATE OF CORRECTION

PATENT NO.       : 6,376,242 B1
APPLICATION NO.  : 09/666224
DATED            : April 23, 2002
INVENTOR(S)      : Stephen R. Hanson It is certified that error appears in the above-identified patent and that said Letters Patent is hereby corrected as shown below:

In claim 1, column 40, line 66, delete "vase" and insert --vaso--.

In claim 24, column 41, line 53, delete "ischemio" and insert --ischemic--.

In claim 26, column 41, line 57, delete "tho" and insert --the--.

In claim 29, column 42, line 7, delete "28" and insert --27--.

In claim 29, column 42, line 13, delete "angloplasty" and insert --angioplasty--.

In claim 47, column 42, line 60, delete "binds" and insert --bind--.

Signed and Sealed this

Twenty-sixth Day of February, 2008

JON W. DUDAS
*Director of the United States Patent and Trademark Office*